US 11,806,439 B2

United States Patent
Lucier et al.

(10) Patent No.: US 11,806,439 B2
(45) Date of Patent: Nov. 7, 2023

(54) MEDICAL STERILIZATION AND STORAGE CABINET WITH MULTIDIRECTIONAL ACCESS

(71) Applicant: Slyder Tray LLC, Creve Coeur, MO (US)

(72) Inventors: Michael J. Lucier, Creve Coeur, MO (US); Kraig H. Allen, Leesburg, IN (US)

(73) Assignee: SLYDER TRAY LLC, Creve Coeur, MO (US)

( * ) Notice: Subject to any disclaimer, the term of this patent is extended or adjusted under 35 U.S.C. 154(b) by 197 days.

(21) Appl. No.: 17/372,742

(22) Filed: Jul. 12, 2021

(65) Prior Publication Data

US 2021/0338874 A1 Nov. 4, 2021

Related U.S. Application Data

(62) Division of application No. 16/236,769, filed on Dec. 31, 2018, now Pat. No. 11,147,896.

(Continued)

(51) Int. Cl.
*A61L 2/00* (2006.01)
*A61L 2/26* (2006.01)
(Continued)

(52) U.S. Cl.
CPC ............ *A61L 2/26* (2013.01); *A61B 17/7074* (2013.01); *A61B 50/10* (2016.02); *A61B 50/33* (2016.02);
(Continued)

(58) Field of Classification Search
CPC ....... A47B 67/02; A61L 2/02; A61L 2202/25; A61L 2/06; A61L 2/07; A61L 2/206; A61B 2050/105; A61B 50/10; A61B 50/33
(Continued)

(56) References Cited

U.S. PATENT DOCUMENTS 5,893,618 A 4/1999 LePage, Jr. et al.
6,164,738 A * 12/2000 Dane .................. A61L 2/26
312/216

(Continued)

FOREIGN PATENT DOCUMENTS

DE 19705137 A1 8/1998
DE 10230545 B4 10/2005
KR 20100081708 A 7/2010

OTHER PUBLICATIONS

International Search Report and Written Opinion for corresponding Application No. PCT/US19/12052 dated May 7, 2019 (11 pages).

(Continued)

*Primary Examiner* — Monzer R Chorbaji
(74) *Attorney, Agent, or Firm* — Dean D. Small; The Small Patent Law Group, LLC

(57) ABSTRACT

Methods, devices and program products are provided for a medical instrumentation storage cabinet. First and second instrumentation retention trays are configured to receive surgical instruments. The housing includes a top plate, a bottom shelf and at least one intermediate shelf there between. The bottom and intermediate shelfs and the first and second instrumentation retention trays include a plurality of holes there through to allow passage of a sterilization medium during a sterilization process. Standoffs are distributed about a perimeter of the housing. The standoffs separate the intermediate shelf from the top plate and bottom shelf to define first and second tray storage areas there between. The first and second tray storage areas have a shape and dimension to receive the first and second instrumentation retention trays. The standoffs are spaced apart from one another to define tray passages there between. The tray passages re sized and located to allow both of the first and second instrumentation retention trays to be inserted into the hous- (Continued)

ing and opened to an open position relative to the housing in at least three directions.

20 Claims, 15 Drawing Sheets

Related U.S. Application Data

(60) Provisional application No. 62/613,290, filed on Jan. 3, 2018.

(51) Int. Cl.
| | | |
|---|---|---|
| *A61L 2/06* | (2006.01) | |
| *A61L 2/07* | (2006.01) | |
| *A61L 2/20* | (2006.01) | |
| *A61B 50/10* | (2016.01) | |
| *A61B 50/33* | (2016.01) | |
| *A61B 17/70* | (2006.01) | |
| *A61L 2/18* | (2006.01) | |
| *A61B 90/00* | (2016.01) | |
| *A61B 50/18* | (2016.01) | |
| *A61B 50/30* | (2016.01) | |

(52) U.S. Cl.
CPC .................................. *A61L 2/06* (2013.01); *A61L 2/07* (2013.01); *A61L 2/206* (2013.01); *A61B 50/30* (2016.02); *A61B 2050/105* (2016.02); *A61B 2050/185* (2016.02); *A61B 2050/3007* (2016.02); *A61B 2090/0813* (2016.02); *A61L 2/18* (2013.01); *A61L 2202/121* (2013.01); *A61L 2202/122* (2013.01); *A61L 2202/17* (2013.01); *A61L 2202/182* (2013.01); *A61L 2202/24* (2013.01)

(58) Field of Classification Search
USPC .................................................. 422/297, 300
See application file for complete search history.

(56) References Cited

U.S. PATENT DOCUMENTS

| | | | |
|---|---|---|---|
| 8,454,901 B1 * | 6/2013 | Snyder, III | ................ A61L 2/26 |
| | | | 422/26 |
| 2004/0032102 A1 | 2/2004 | Safari et al. | |
| 2009/0121591 A1 | 5/2009 | Giese et al. | |
| 2011/0291372 A1 | 12/2011 | Stryker et al. | |

OTHER PUBLICATIONS

Extended European Search Report for related European Patent Application No. 19736127 dated Sep. 6, 2021 (9 pages).

* cited by examiner

MEDICAL STERILIZATION AND STORAGE CABINET WITH MULTIDIRECTIONAL ACCESS

RELATED APPLICATION

The present application is a divisional application of U.S. application Ser. No. 16/236,769, titled "MEDICAL STERILIZATION AND STORAGE CABINET WITH MULTIDIRECTIONAL ACCESS" filed 31 Dec. 2018, which claims priority from U.S. Application No. 62/613,290, titled "MEDICAL STERILIZATION AND STORAGE CABINET WITH MULTIDIRECTIONAL ACCESS" filed 3 Jan. 2018, the full and complete subject matter of which are expressly incorporated herein by reference in their entirety.

BACKGROUND

Embodiments of the present disclosure generally relate to medical instrumentation containers and more specifically to medical sterilization storage cabinets.

In the 1980s, sterilization container systems and surgical trays were generally introduced in the U.S. The container systems and surgical trays varied in design, mechanics and construction materials. Today, these container systems utilize various packaging options to organize and utilize surgical instruments. Rigid reusable sterile container systems are used for the packaging, transportation, and storage of instruments prior to, during, and after sterilization. The container systems include a broad line of products including lids and bottoms in various sizes, with assorted accessories such as baskets, filters, clamps, organization tools, containment devices, and tamper evident locks. Reusable rigid sterile containers offer some advantages over other packing options, such as wrap and peel pouches. For example, the rigid sterile containers may provide economic and environmental benefits, along with increased safety.

However, conventional container and tray systems experience certain limitations. In an operating room, nurses and/or surgical team members seek to deliver instruments and implants to the surgeon in a timely and efficient manner. However, surgical procedures can extend over several hours and involve the user of a large number of different surgical instruments. Surgical procedures are unpredictable and the nurses and/or surgical team are not able to anticipate which instrumentation the surgeon will need next. Also, multiple nurses/team members participate in providing instruments to the surgeon. As one example, new nurses and team members may enter a surgical room at intermediate points during the procedure and supplement or take over for other nurses who start the procedure. Procedure length, complexity, and staff changes render it difficult to keep track of the instruments and assist a surgeon in the most efficient manner.

An operating room environment has limited table space and therefore it is not practical to neatly set out all of the surgical instruments that may be needed during the procedure. Instead, the conventional container systems generally resemble a large suitcase or briefcase with an open top and with numerous trays stacked upon one another. At the beginning of the procedure, the trays are removed from the container and the container is placed to the side. The trays are spread out on tables. Given that one procedure may involve numerous surgical instruments, multiple trays of instruments are spread across the limited table space. The trays are also stacked upon one another in a generally un-organized manner. When an instrumentation from a lower tray in a stack is needed, the trays upon the tray of interest are moved and re-stacked upon other trays. This pattern of moving and re-stacking instruments trays results in a cluttered and disorganized assembly of trays and loosely organized instruments spread about the surgical environment. Consequently, it becomes difficult for nurses/team members to locate individual instruments in a timely and efficient manner when requested by the surgeon, which can slow down the procedure and efficiency in the environment.

Moreover, during an operating room procedure, conventional instrumentation trays are taken out of any sterile container and spread/distributed across any available table space within the operating room. Additionally or alternatively, a large number of the instruments within the trays may be removed from the trays during the preparation of the operating room with the estimates being laid out upon tables within the operating room. It is desirable to lay out as many of the instruments as practical and/or spread out as many instrumentation trays as possible in order that the clinicians may see the available instruments and have ready access thereto without stacking and unstacking numerous instrumentation trays in the middle of a procedure.

However, while an operating room is generally a sterile environment, numerous contaminants are introduced throughout the room during a medical procedure. Instruments that are exposed to the operating room environment are similarly exposed to such contaminants. The longer that instruments are exposed to the operating room environment, the greater the level contaminants collected by the instrumentation and/or the greater the risk that the instrumentation will collect and unduly high level of contaminants. Medical instrumentation contamination remains a substantial concern within the medical profession.

SUMMARY

In accordance with embodiments herein, a medical instrumentation storage cabinet is provided that comprises: first and second instrumentation retention trays configured to receive surgical instruments; a housing including a top plate, a bottom shelf and at least one intermediate shelf there between, one or more of the top plate, the bottom shelf, the intermediate shelf or the first and second instrumentation retention trays including a plurality of holes there through to allow passage of a sterilization medium during a sterilization process; and the housing separating the intermediate shelf from the top plate and bottom shelf to define first and second tray storage areas there between, the first and second tray storage areas configured to receive the first and second instrumentation retention trays, respectively; and tray passages provided in the housing, the tray passages located to allow both of the first and second instrumentation retention trays to be inserted into the housing and opened to an open position relative to the housing in at least three directions.

In accordance with embodiments herein, a method of providing a medical instrumentation storage cabinet is provided that comprises: configuring first and second instrumentation retention trays to receive surgical instruments; providing a housing including a top plate, a bottom shelf and at least one intermediate shelf there between, one or more of the top plate, the bottom shelf, the intermediate shelf or the first and second instrumentation retention trays including a plurality of holes there through to allow passage of a sterilization medium during a sterilization process; and separating the intermediate shelf from the top plate and bottom shelf to define first and second tray storage areas there between, the first and second tray storage areas configured to receive the first and second instrumentation retention trays, respectively; and locating tray passages about a perimeter of the housing to allow both of the first and second instrumentation retention trays to be inserted into the housing and opened to an open position relative to the housing in at least three directions.

In accordance with an embodiment, a medical sterilization and storage cabinet is provided with a new and convenient manner to access instruments within the storage cabinet while in a variety of healthcare settings from the operating room theatre, emergency room settings, hospital rooms, ambulatory surgery centers, doctors' offices, dental clinics and the like. In accordance with embodiments herein, a sterilization cabinet is provided that affords a unique and flexible storage solution system to organize and house surgical trays and instruments in trays that the medical staff can readily access without stacking and unstacking trays, while also providing the capability for the trays to open in multiple directions. The trays are reusable, rigid, sterile containers that can withstand numerous autoclave processes. In accordance with embodiments herein, a sterilization and storage cabinet is provided that affords a new solution for manufacturers of healthcare equipment who are looking for the next generation of surgical tray and instrumentation management.

Among other things, the sterilization and storage cabinets described herein reduce the potential for contamination as compared to conventional instrumentation storage systems. The sterilization and storage cabinets retain trays in a closed position, in which the open top of the tray is enclosed within the cabinet and generally isolated from the environment within the operating room or other clinical area. The trays may be retained enclosed in a sheltered environment within the cabinet for a substantial portion of the medical procedure, only opening the trays at or near the time when the instruments therein are to be used. By reducing the amount of time in which the instruments are exposed to the environment of the operating room or other clinical area, embodiments herein substantially reduce the exposure time to contaminants within the environment and substantially reduce the level of contamination experienced by such instruments prior to usage.

The sterilization and storage cabinet offers cost effective, convenient solutions to a variety of healthcare markets. Additionally, the sterilization and storage cabinet can be sterilized with blue-wrap or used with rigid containers, with market segment by application divided between hospitals with emergency/operating rooms and other medical institutions such as urgent care clinics and dental care offices. The sterilization and storage cabinet herein provides a packaging option which provides a cost effective, efficient organization and utilization of surgical instruments and trays. A sterilization and storage cabinet is provided that affords a durable, long-lasting, reusable packaging system for sterilization, storage, and transport of medical devices. A sterilization and storage cabinet is provided that affords a new, innovative, convenient, multi-directional, removable, more flexible and efficient access to storage trays and instruments in a limited space environment with the flexibility to be "blue wrapped" or used with available rigid containers. The multidirectional drawer system allows ease of use in tight areas, offers an ability to organize surgical instrumentation space, and maintains sterility. Embodiments herein provide a design that protects surgical instruments with a hard and sheltered structure. Embodiments herein provide an ergonomic design and handling system that enables proper, easy and safe transportation.

In accordance with embodiments herein, a medical instrumentation storage cabinet is provided that comprises first and second instrumentation retention trays configured to receive surgical instruments; a housing including a top plate, a bottom shelf and at least one intermediate shelf there between, one or more of the top plate, the bottom shelf, the intermediate shelf or the first and second instrumentation retention trays including a plurality of holes there through to allow passage of a sterilization medium during a sterilization process; and standoffs distributed about a perimeter of the housing, the standoffs separating the intermediate shelf from the top plate and bottom shelf to define first and second tray storage areas there between, the first and second tray storage areas configured to receive the first and second instrumentation retention trays, respectively. The standoffs are spaced apart from one another to define tray passages there between, the tray passages sized and located to allow both of the first and second instrumentation retention trays to be inserted into the housing and opened to an open position relative to the housing in at least three directions.

Optionally, the first and second instrumentation retention trays have a baseplate and walls at least partially surrounding the baseplate, the baseplate configured to receive surgical instruments, the walls having a height that corresponds to a height of the first and second storage areas. Optionally, the at least three directions include at least one side and opposite ends of the housing. Optionally, the at least three directions include at least one end and opposite sides of the housing. Optionally, the standoffs are spaced apart to define tray passages in four directions including both sides and both ends of the housing. Optionally, the top plate, bottom and intermediate shelfs and first and second instrumentation retention trays are formed of a sterilization tolerant material. Optionally, one or more of the top plate, and bottom and intermediate shelfs include tabs distributed about the perimeter, the tabs extending in a transverse direction to at least partially form the standoffs that separate the intermediate shelf from the top and bottom shelfs. Optionally, the cabinet may further comprise a bracket connector joined to corners of the top plate, bottom shelf and intermediate shelfs to at least partially form the standoffs.

At least one of the first and second instrumentation retention trays may include feet provided on a bottom surface thereof, the feet separating the bottom surface from a top surface of the corresponding adjacent bottom and/or intermediate shelf to allow lateral distribution of the sterilization medium during the sterilization process. The top plate and bottom shelf may include rails formed along side and end edges thereof, the rails on the top plate facing and aligning with the rails on the bottom shelf, the housing further comprising side and end doors slidably received within the corresponding rails, the side and end doors sliding between open and closed positions to expose and cover the side and end tray passages. The rails along one or more of the sides and ends of the housing include a door retention segment configured to retain a corresponding side and end door when in an at least partially open position, the side and end doors having front bottom edges configured to engage a surface on which the cabinet is positioned while the door retention segments retain a rear segment of the side and end doors to form a counterbalance lever to resist tipping by the housing when one or more of the first and second instrumentation retention trays is partially removed from the corresponding first or second tray retention area.

Optionally, the first and second tray storage areas have heights that substantially match heights of the first and second instrumentation retention trays, respectively, such that the housing supports the first and second instrumentation retention trays when opened to a fully open position. Optionally, the cabinet may further comprise third, fourth and fifth instrumentation retention trays, wherein the first through fifth instrumentation retention trays are independently insertable and openable relative to the housing in the at least three directions.

In accordance with embodiments herein, a method is provided of providing medical instrumentation storage cabinet. The method comprises configuring first and second instrumentation retention trays to receive surgical instruments; providing a housing including a top plate, a bottom shelf and at least one intermediate shelf there between, one or more of the top plate, the bottom shelf, the intermediate shelf or the first and second instrumentation retention trays including a plurality of holes there through to allow passage of a sterilization medium during a sterilization process; distributing standoffs about a perimeter of the housing, the standoffs separating the intermediate shelf from the top plate and bottom shelf to define first and second tray storage areas there between, the first and second tray storage areas configured to receive the first and second instrumentation retention trays, respectively; spacing the standoffs apart from one another to define tray passages there between; and sizing and locating the tray passages to allow both of the first and second instrumentation retention trays to be inserted into the housing and opened to an open position relative to the housing in at least three directions.

Optionally, the first and second instrumentation retention trays have a baseplate and walls at least partially surrounding the baseplate, the method further comprising inserting surgical instruments on the baseplate, the walls having a height that corresponds to a height of the first and second storage areas. Optionally, the method may comprise inserting and/or opening the first instrumentation retention tray through one side, inserting and/or opening the first instrumentation retention tray through a first end of the housing and inserting and/or opening the first instrumentation retention tray through an opposite second end of the housing. Optionally, the method may comprise inserting and/or opening the first instrumentation retention tray through a first side of the housing, inserting and/or opening the first instrumentation retention tray through a second side of the housing and inserting and/or opening the first instrumentation retention tray through an end of the housing.

Optionally, the method may comprise inserting and/or opening the first instrumentation retention tray through a first side of the housing, inserting and/or opening the first instrumentation retention tray through a second side of the housing and inserting and/or opening the first instrumentation retention tray through an end of the housing; and inserting and/or opening the second instrumentation retention tray through the first side of the housing, inserting and/or opening the second instrumentation retention tray through the second side of the housing and inserting and/or opening the second instrumentation retention tray through the end of the housing. Optionally, the method may comprise forming the top plate, bottom and intermediate shelfs and first and second instrumentation retention trays of a sterilization tolerant material. Optionally, the method may comprise loading the first and second instrumentation retention trays with instrumentation, inserting the first and second instrumentation retention trays into corresponding first and second tray storage areas and loading the cabinet into a chamber and introducing a sterilization medium to the chamber, the sterilization medium propagates through interior passages within the cabinet to sterilize surfaces of the cabinet. Optionally, the method may comprise maintaining a space between the first and second instrumentation retention trays and bottom and intermediate shelfs to define air passages that allow a sterilization medium to touch upper and lower surface of the first and second instrumentation retention trays and bottom and intermediate shelfs. The sterilization medium is at least one of heated air, steam, liquid or vapor chemicals. Optionally, the method may comprise organizing instrumentation within the first and second instrumentation retention trays based on a predetermined procedure such that a first set of instrumentation in the first instrumentation retention tray corresponds to a first aspect of the predetermined procedure and a second set of instrumentation in the second instrumentation retention tray corresponds to a second aspect of the predetermined procedure. Optionally, the method may comprise marking the first and second instrumentation retention trays with indicia indicative of a content thereof, wherein the indicia indicate at least one of color coding, descriptive text, or numbers. Optionally, the method may comprise partially opening a door on one or more side or end of the cabinet and retaining a portion of the door in rails in the cabinet, the door forming a counterbalance lever to resist tipping by the housing when one or more of the first and second instrumentation retention trays is partially removed from the corresponding first or second tray retention area.

In accordance with embodiments herein, a method is provided that comprises: providing a collection of multi-level cabinets that include stage-1 and stage-2 multi-level cabinets for use in connection with at least first and second stages, respectively, of a surgical procedure, each of the stage-1 and stage-2 cabinets comprising: a housing including a top plate, a bottom shelf and at least one intermediate shelf there between, the housing separating the intermediate shelf from the top plate and bottom shelf to define first and second tray storage areas there between, the first and second tray storage areas configured to receive the first and second instrumentation retention trays, respectively; and tray passages located on at least a side and an end of the housing and communicating with the first and second tray storage areas to allow both of the first and second instrumentation retention trays to be inserted into the housing and opened to an open position relative to the housing in at least two directions; providing the stage-1 cabinet with instrumentation retention trays loaded with instrumentation for use with actions or tasks performed during the first stage of the surgical procedure; and providing the stage-2 cabinet with instrument retention trays loaded with instrumentation for use with actions or tasks performed during the second stage of the surgical procedure.

In accordance with embodiments herein, the providing the stage-1 and stage-2 cabinets comprises loading the instruments in the instrumentation retention trays and loading the instrumentation retention trays into the stage-1 and stage-2 cabinets. Optionally, the providing the stage-1 and stage-2 cabinets comprises stacking the stage-1 and stage-2 cabinets in an operating room environment. Optionally, the method further comprising: utilizing the collection of multi-level cabinets during the surgical procedure; opening the instrument retention trays of the stage-1 cabinet during the first stage while maintaining the instrument retention trays of the stage-2 cabinet closed in an enclosed and sheltered environment during the first stage. Optionally, the method further comprising maintaining the instrument retention trays of the stage-1 and stage-2 cabinets closed in an enclosed and sheltered environment until one or more of the instruments in a corresponding one of the instrument retention trays is needed for use in the surgical procedure to reduce a potential for contamination. Optionally, the surgical procedure includes an exposure stage, a screw insertion stage and a rod manipulation stage, the multi-level cabinets including at least one instrument retention tray that includes rod manipulation instruments for use during the rod manipulation stage, the method further comprising maintaining the at least one instrument retention tray, that includes the rod manipulation instruments, in an enclosed and sheltered environment within the corresponding multi-level cabinet until the surgical procedure advances to the rod manipulation stage. Optionally, the at least two directions include at least one end and at least one side of the housing. Optionally, the tray passages in the stage-1 cabinet are positioned to allow the instrumentation retention trays therein to be inserted into the housing and opened to an open position relative to the housing through at least one end and at least one side, wherein the tray passages in the stage-2 cabinet are positioned to allow the instrumentation retention trays therein to be inserted into the housing and opened to an open position relative to the housing through at least one end and at least one side. Optionally, the tray passages in the stage-1 and stage-2 cabinets are positioned to allow the instrumentation retention trays therein to be inserted into the corresponding housings and opened to an open position relative to the corresponding housings through at least three directions.

In accordance with embodiments herein, a medical instrumentation storage cabinet system is provided comprising: a collection of multi-level cabinets that include stage-1 and stage-2 multi-level cabinets for use in connection with at least first and second stages, respectively, of a surgical procedure, each of the stage-1 and stage-2 cabinets comprising: a housing including a top plate, a bottom shelf and at least one intermediate shelf there between, the housing separating the intermediate shelf from the top plate and bottom shelf to define first and second tray storage areas there between, the first and second tray storage areas configured to receive the first and second instrumentation retention trays, respectively; and tray passages located on at least a side and an end of the housing and communicating with the first and second tray storage areas to allow instrumentation retention trays to be inserted into the housing and opened to an open position relative to the housing in at least two directions.

Optionally, the instrumentation retention trays, in the stage-1 cabinet, are loaded with instrumentation for use with actions or tasks performed during the first stage of the surgical procedure; and the instrumentation retention trays, in the stage-2 cabinet, are loaded with instrumentation for use with actions or tasks performed during the second stage of the surgical procedure. Optionally, the tray passages in at least on of the stage-1 or stage-2 cabinets are located to allow the instrumentation retention trays to be inserted into the housing and opened to an open position relative to the housing in at least three directions. Optionally, the stage-1 and stage-2 cabinets are stacked on one another. Optionally, one or more of the top plate, the bottom shelf, the intermediate shelf or the instrumentation retention trays include a plurality of holes there through to allow passage of a sterilization medium during a sterilization process. Optionally, the tray passages are configured to allow the instrument retention trays of the stage-1 cabinet to be open during the first stage while maintaining the instrument retention trays of the stage-2 cabinet closed in an enclosed and sheltered environment during the first stage.

DETAILED DESCRIPTION

Figure 1A:
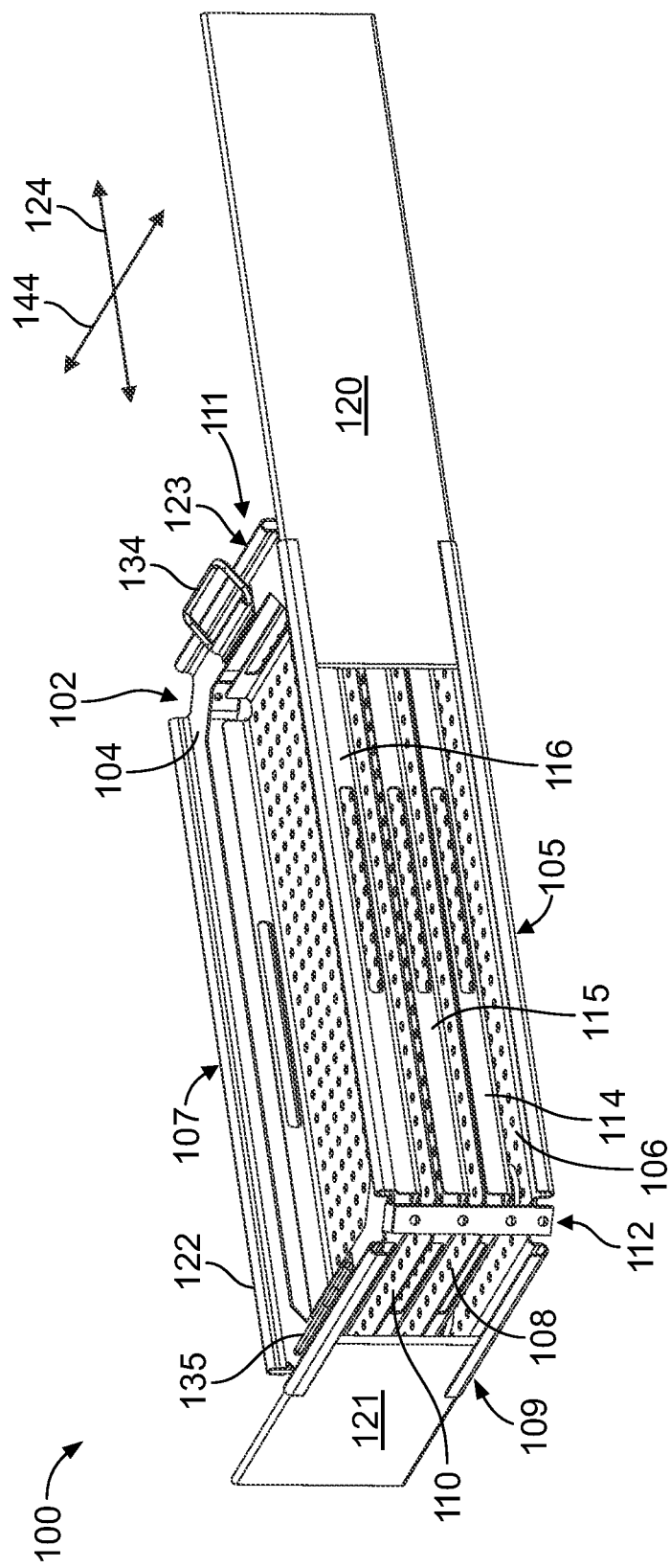
FIG. 1A illustrates a partially open perspective view of a medical instrumentation storage cabinet formed in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Throughout the present description, the terms "front", "back", "side", "end", "forward", "rear", and "rearward" are used as relative terms with respect to a reference perspective. The reference perspective may be defined by one or more of i) an orientation of a cabinet while positioned on a table or other support surface, such as during a cleaning process or medical procedure, ii) a surface of the cabinet facing and in closest proximity to medical personnel during cleaning, loading, or a medical procedure, iii) an orientation in which medical instruments are stored in the cabinet, and/or iv) a shape of the cabinet. For example, when the cabinet is shaped in an elongated configuration, such as with a rectangular, elliptical or oval shape, the cabinet would generally include a longitudinal axis extending along a length of the cabinet and a transverse axis. By way of example, the "sides" of the cabinet may represent the surfaces that extends generally parallel to the longitudinal axis, while the "ends" of the cabinet may represent the surfaces of the cabinet that extend generally parallel to the transverse axis. The term "side" may be used to collectively refer to either or both of the front and back surfaces of the cabinet. The sides and ends of the cabinet may be defined simply based upon the manner in which the cabinet is oriented when the cabinet is positioned on a table or other supporting surface during cleaning, loading, or a medical procedure. The cabinet may be positioned in various orientations depending upon the available table space. When a cabinet is placed on a table, the surface of the cabinet facing the medical personnel and in closest proximity to the medical personnel would represent the front. As another example, the reference perspective may be defined based on the orientation of the medical instruments when stored. For example, the instruments may be loaded into a tray with bottom ends of the instruments facing one wall of the tray. When the trays are loaded into the cabinet, the surface of the cabinet, toward which the bottom ends of the instruments face may represent a "front" or "back" depending upon the direction in which the medical personnel prefer the instruments to be oriented.

The terms "autoclave" and "autoclaving" refer to sterilization systems and processes to process medical instruments in a pressurized vessels which require exposure to elevated pressure and temperature.

The term "instrumentation" includes, but is not limited to, instruments, implants, trial implants and the like.

The term "sterilization process" refers to any process utilized to clean and sterilize medical instruments by an amount accepted by an appropriate medical body or as defined by a corresponding standards body. As a non-limiting example, an autoclave system may be used in a sterilization process. As another example, steam may be used for sterilizing instruments, trays, and cassettes. According to the Center for Disease Control and Prevention, steam under pressure is at least one process of choice whenever possible as it is considered safe, fast, and the cost-effective for health care facilities.

The term "sterilization tolerant material" refers to materials that may be utilized to form components of the cabinet described herein where such materials are able to withstand repeated exposure to the temperatures, pressures, chemicals and other environmental characteristics to which the cabinet is exposed during a sterilization process. Non-limiting examples of sterilization tolerant materials include aluminum and stainless steel. Other non-limiting examples of sterilization tolerant materials include certain high-performance polymers, such as the Radel® polyphenylsulfone (PPSU) materials by Solvay Specialty Polymers of Alpharetta, Ga.

The term "surgical procedure setting" refers to any room or area utilized for a surgical procedure, including but not limited to an operating room, emergency room, hospital patient room, ambulatory surgery centers, doctors' offices, dental clinics and the like. The terms "open position" and "open state" refer to a position of a tray relative to the cabinet, in which a leading section of the tray is exposed from the cabinet while a trailing section of the tray remains held within the cabinet.

The term "fully open" refers to a position in which a tray is opened to expose at least 90% of an instrumentation storage area within the tray, while no more than 10% of the instrumentation storage area within the tray remains covered within the cabinet.

The term "removed position" refers to a tray position in which the tray is entirely separated and removed from the cabinet.

FIG. 1A illustrates a partially open perspective view of a medical instrumentation sterilization and storage cabinet 100 formed in accordance with embodiments herein. The medical instrumentation storage cabinet 100 includes a housing 102 that includes a series of stacked component layers (generally referred to as plates and shelves) that are rigidly affixed to one another and that are configured to slidably receive multiple instrumentation retention trays. As explained herein, the housing 102 is constructed to enable the instrumentation retention trays to be inserted and removed (partially or wholly) in multiple directions. For example, trays may be pulled out until 50%, 75%, 90% of the tray is exposed. Separate trays may be pulled out partially from the one or both sides and one or both ends to expose the content of three or four trays simultaneously while the trays are supported by the cabinet 100.

The housing 102 includes sides 105, 107 that extend parallel to a longitudinal axis 124 and ends 109, 111 that extend parallel to a transverse axis 144. The longitudinal and transverse axes 124, 144 are provided as non-limiting references and should not be interpreted to limit the shape or dimensions of the cabinet 100 in any manner. In the example of FIG. 1A, the cabinet 100 is formed in a generally rectangular shape, a length of which extends along the longitudinal axis 124 and a width of which extends along the transverse axis 144. It is recognized that the cabinet 100 may be formed in numerous alternative shapes. As non-limiting examples, the cabinet may be configured with a rectangular shape, a triangular shape, a circular shape, an elliptical or oval shape, a trapezoidal shape, and the like.

During a medical procedure, once the doors 120, 121 are removed, the individual trays 114-116 may remain enclosed within the cabinet 100 until a desired instrumentation is needed therefrom. Once an instrumentation is removed from an individual tray 114, 116, the tray may be returned to the closed position and/or may remain open depending upon whether additional instruments in the tray are expected to be needed in the near future within the procedure. The cabinet 100 allows an easy mechanism for accessing trays and thus affords an equally easy mechanism for the user to close a tray after an individual instrumentation is removed. Consequently, in an effort to limit contamination, operating room personnel would be able to close a tray once an individual instrumentation is removed, and not necessarily leave all of the trays open and distributed across tables within the operating room. The operating room personnel could open and close the trays repeatedly throughout the procedure, without slowing down the procedure or experiencing difficulty in locating particular instruments, and thus would substantially reduce the amount of time that clean unused instruments are exposed to the operating room general environment. Consequently, by providing a cabinet that readily allows access to trays, even while stacked, embodiments herein facilitate a manner of contamination conscious management that retains clean unused instruments in an enclosed environment (generally isolated from contamination in the operating room) until such instruments are needed.

Figure 1B:
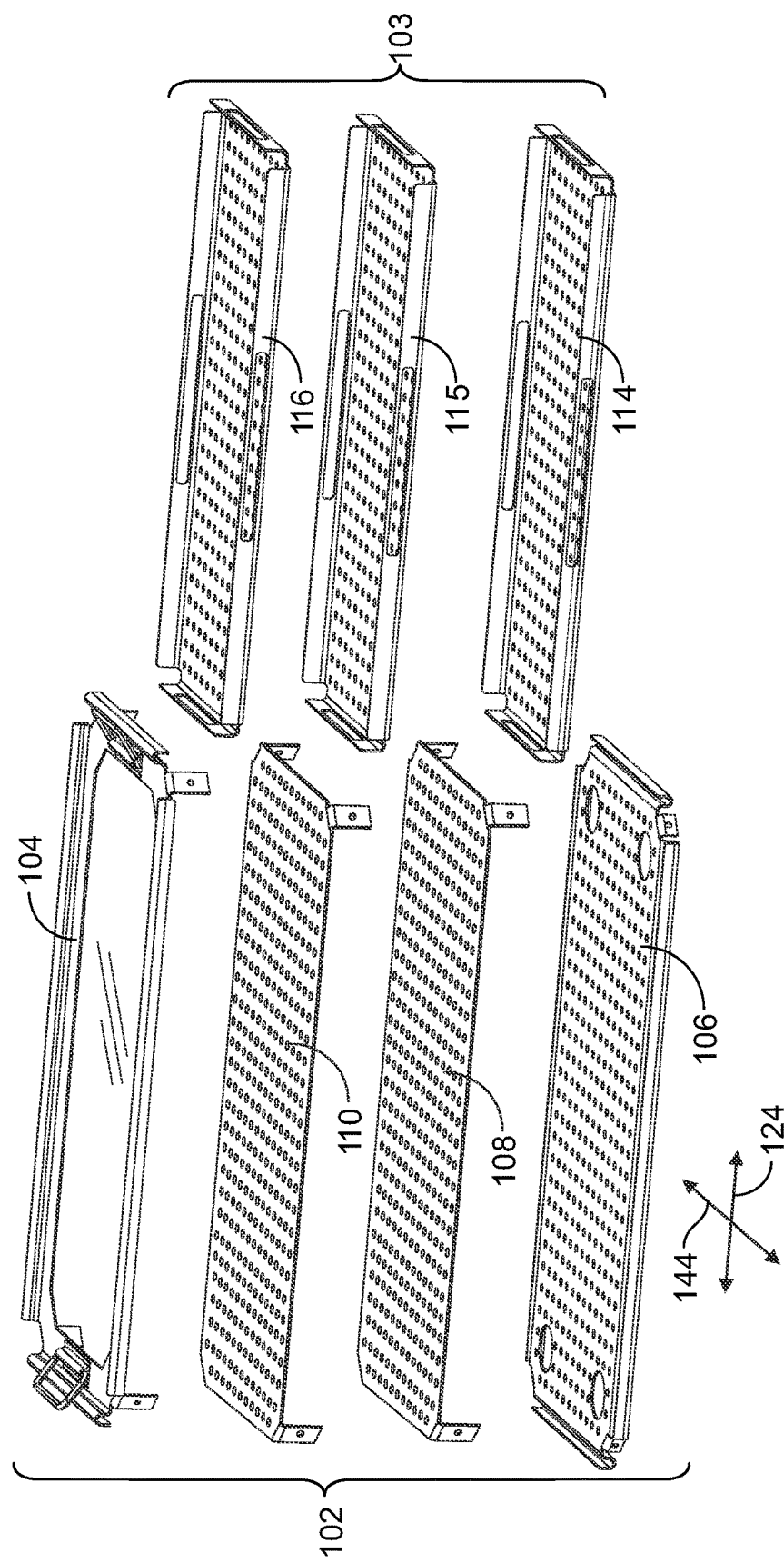
FIG. 1B illustrates the various components of the housing and a set of instrumentation retention trays.

FIG. 1B illustrates the various components of the housing 102 and a set 103 of instrumentation retention trays 114-116. The housing 102 includes top plate 104, bottom shelf 106 and at least one intermediate shelf 108 there between. In the example of FIGS. 1A and 1B, first and second intermediate shelves 108, 110 are provided. The housing 102 slidably receives instrumentation retention trays 114-116. As explained hereafter, the housing 102 is configured to allow the instrumentation retention trays 114-116 to be inserted into and removed from the housing 102 in at least three distinct tray access directions. The tray access directions are described relative to the longitudinal axis 124 and transverse axis 144. For example, the three distinct directions may be any combination from the sides 105, 107 and ends 109, 111 of the housing 102. In the example of FIG. 1, two intermediate shelves 108, 110 are provided, although it is recognized that the housing 102 may be formed with a single intermediate shelf or more than two intermediate shelves, to provide cabinet 100 with different numbers of instrumentation retention trays. For example, the cabinet 100 may be formed to hold only two trays (e.g., 115 and 116), such as by including shelves 106 and 108, and removing shelf 110. Additionally or alternatively, multiple cabinets 100 may be stacked on top of one another. For example, 2, 3 or more cabinets 100 may be stacked on one another, where each of the cabinets 100 may be formed to include 2, 3 or more trays. Each cabinet 100 in the stack may have the same or a different number of trays. The heights of various cabinets 100 may be varied, such that a first cabinet 100 is taller than a second cabinet 100. Optionally, the shelves 106, 108, 110 and trays 114-116 may be formed with different heights. For example, the space associated with the lowest shelf 106 and tray 114 may have greater height than the top shelf 110 and tray 116, or vice versa.

The component layers within the cabinet 100, such as the top plate 104, shelves 106, 108, 110 and instrumentation retention trays 114-116, are formed of a sterilization tolerant material. By way of example only, one or more of the top plate 104, bottom shelf 106, shelves 108, 110 and instrumentation retention trays 114-116 may be formed of stainless steel, aluminum, or Radel® R material. Optionally, different combinations of materials may be utilized. For example, the shelves 106, 108, 110 may be formed from aluminum, while the trays 114-116 may be formed from plastic or Radel® R material. Optionally, the component layers are FDA compliant for use in gravity or pre-vacuum steam and ETO sterilization. Optionally, the component layers may be compatible with CSR wrap and filtered containers. All of the component layers within the cabinet 100 may be formed of a common material. Alternatively, some of the component layers within the cabinet 100 may be formed of one material, while other component layers within the cabinet 100 may be formed of another material. For example, the top plate 104 and shelves 106, 108, 110 may be formed of stainless steel, while the instrumentation retention trays 114-116 may be formed of aluminum, and vice versa. As another example, the top plate 104 and shelves 106, 108, 110 may be formed of one material, while the instrumentation retention trays 114-116 may be formed of another material, and vice versa. Optionally, any one or more of the components may be formed of a combination of materials. Optionally, the sterilization tolerant material(s) used to form the components of the cabinet 100 may also be biocompatible materials. The top plate 104 and bottom shelf 106 and shelves 108, 110 may be formed in various manners, such as stamp and forming, molding, machining, extrusion and the like. The parts of any one or more of the top plate 104 and bottom shelf 106 and shelves 108, 110 discussed herein may be formed with one another as one monolithic structure. Optionally, the parts may be manufactured separated and assembled to one another.

Standoffs 112 are positioned at distributed points about a perimeter of the housing 102. The standoffs 112 are secured to and separate the intermediate shelves 108, 110, the top plate 104 and bottom shelf 106. The standoffs 112 hold the shelves 106, 108, 110 and top plate 104 spaced apart from one another in order to define tray storage areas there between. In the example of FIG. 1, first and second tray storage areas are provided and have a shape (e.g., height, longitudinal length and transverse length) to receive and retain corresponding first and second instrumentation retention trays 114-116 in a secure manner.

Returning to FIG. 1A, the standoffs 112 are spaced apart from one another about the perimeter of the housing 102 to define tray passages between adjacent standoffs 112. In the present example, the tray passages are located at one or more sides (e.g., front and/or back) and at opposite ends of the housing 102. The tray passages are sized to allow the first instrumentation retention tray 114 to be inserted into and removed from the housing 102 in multiple directions, including through all three of the one or more sides 105, 107 (e.g., front and/or back) and opposite ends 109, 111 of the housing 102. In addition, the tray passages are positioned and sized to allow the second instrumentation retention tray 116 to also be inserted into and removed from the housing 102 in multiple directions, including through three or more of the sides 105, 107 and ends 109, 111 of the housing 102. Additionally or alternatively, the tray passages may be positioned and sized to allow one or both of the first and second instrumentation retention trays 114, 116 to be inserted into and removed from the housing 102 through four directions including both sides 105, 107 and both ends 109, 111 of the housing 102. The height of the tray storage areas is substantially similar to a height of the corresponding instrumentation retention trays 114-116, provided sufficient tolerance is included to allow the trays 114-116 to fully slide in and out of the cabinet 100. The height tolerance is maintained relatively close such that, when a tray 114-116 is partially pulled out, the remaining tail section of the tray 114-116 is held firmly between adjacent shelves 106, 108, 110 and/or top plate 104. The tail sections of the tray 114-116 forms a base of a cantilevered arm to support and maintain the exposed leading section of the tray 114-116. By way of example, a substantial majority (e.g., 75-95%) of the trays 114-116 may be pulled outward to an exposed state while a relative small (e.g., 10-5%) tail section forms the base of the cantilevered arm.

As explained in more detail hereafter, doors 120-123 are provided over the sides 105, 107 and ends 109, 111 of the housing 102. The doors 120-123 slide within rails (described below in more detail) between open and closed positions. The doors may be moved to a partially open position, as well as entirely removed from the housing 102 and placed elsewhere while a procedure is performed and instruments are being removed from and replaced within the cabinet 100. The doors 120-123 may be formed of the same material as the component layers of the cabinet 100. Additionally or alternatively, one or more of the doors 120-123 may be formed of a transparent material, such as to allow for easy visualization of labels provided on individual shelves. For example, the end and/or sidewalls of the trays may include labels designating the general nature of the content or listing the individual instruments therein. By utilizing transparent doors, a user may easily read the labels through the doors without opening the doors. Optionally, the doors 120-123 may include holes (not illustrated) similar to the holes in the trays and shelfs.

The housing 102 includes handles 134, 135 provided on the top plate 104. The handles 134, 135 facilitate carrying of the cabinet 100. Optionally, the handles 134, 135 may be removed entirely, located in other positions and/or replaced/supplemented with additional handles.

Figure 2:
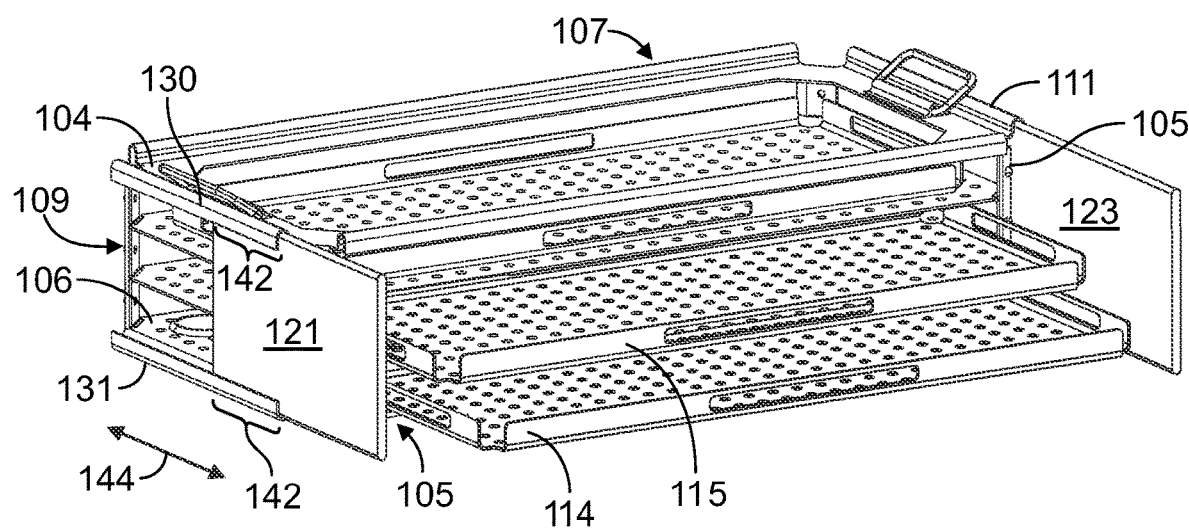
FIG. 2 illustrates a top front perspective view of the cabinet with the side door and the side door slid within corresponding rails to a partially open position.

FIG. 2 illustrates a top front perspective view of the cabinet 100 with the end door 121 (also referred to as a front door) and the end door 123 (also referred to as a back door) slid within corresponding rails to a partially open position. The side door 120 has been entirely removed to expose the tray passages through the corresponding side of the housing 102. The instrumentation retention tray 114 has been slid outward along the transverse axis 144 from the corresponding tray passage in the side 105 of the housing 102 to a fully open position. As illustrated in FIG. 2, the instrumentation retention tray 115 is slid outward to a partially open position, although it is recognized that all of the instrumentation retention tray 114-116 may be slid further out until entirely separated from the housing 102. The top plate 104 and bottom shelf 106 include sets of rails provided along the sides 105, 107 and ends 109, 111 of the housing 102. The rails on the top plate 104 face and align with rails on the bottom shelf 106. In the example of FIG. 2, top and bottom side rails 130, 131 are labeled and slidably receive the door 121 and allow the door 121 to be slid between open and closed positions (with a partially open position illustrated in FIG. 2). End door 123 is moved in a similar manner. The top plate 104 to be formed of a transparent material. The top plate 104 may be removable. Optionally, the top plate 104 may be provided with a hinge along one or more sides and/or ends to allow the top plate 104 to be pivotally opened for access to the top tray.

In generally, tipping would not occur in most circumstances. Instead, a center of gravity of the cabinet 100 would remain at a stable point. For example, the empty weight of the cabinet 100 may be sufficient to offset any imbalance created when multiple trays are opened in a common direction. Additionally or alternatively, the instruments may be loaded in a manner to facilitate balance such as by loading heavier instruments in the lower trays or in trays that are typically entirely removed and not simply pulled out to an open suspended position.

Optionally the doors 120-123 may be used as legs to resist tipping. The top and bottom side rails 130, 131 include door retention segments, such as an outermost segments 142, that cooperate with the door 120. When the door 120 is in a partially open position the door 120 forms a leg to resist tipping by the housing 102. For example, the instrumentation retention trays 114, 116 may all be opened to a fully open state from the corresponding tray storage area. In the example of FIG. 2, the segments 142 are located at opposite ends of each rail 130, 131, such that regardless of the direction in which the side door 120 is opened, a trailing portion of the side door 120 may be retained within the segment 142 to resist tipping of the housing 102 in either direction along the transverse axis 144. While not separately illustrated in FIG. 2, it is recognized that the rails along opposite side of the top plate 104 and bottom shelf 106 also include door retention segments similar to the segments 142. The end doors 121, 123 may be slid in either direction along the transverse axis 144 within the corresponding rails to expose the corresponding end of the housing 102. The end doors 121, 123 may be slid along the transverse axis 144 until only a tail portion of the door remains within the door retention segment of the corresponding rail in order to resist tipping of the housing 102 in either direction along the transverse axis 144, such as when one or more instrumentation retention trays is partially pulled out through the front or back of the housing 102. Optionally, the rails 130, 131 may be manufactured separately from the shelfs and then attached to the shelfs through various means.

Figure 3:
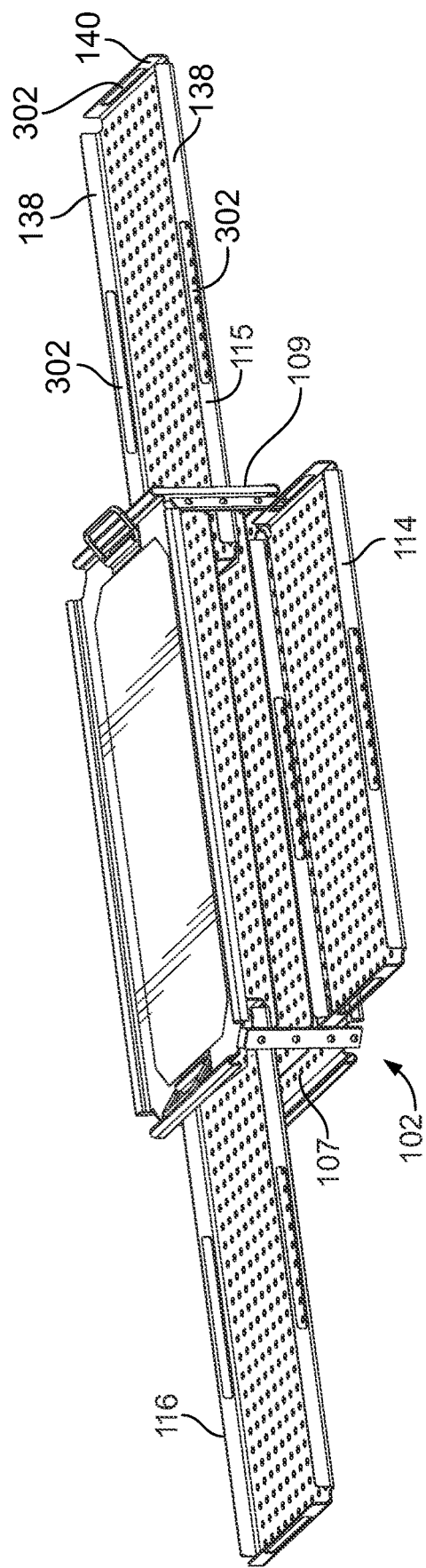
FIG. 3 illustrates a top front perspective view of the cabinet with the side door partially open and the end door slid fully open.

FIG. 3 illustrates a top front perspective view of the cabinet 100. The doors 120-123 has been entirely removed from the corresponding rails in the top plate 104 and bottom shelf 106 to entirely expose the ends and sides of the housing 102. The instrumentation retention trays 114-116 are pulled outward in three opposite directions, namely from opposite ends and one side of the cabinet 100. Each of the trays 114-116 include handle features 302 provided along each of the side and end walls 138, 140. For example, the handle features 302 may be formed as notches or slots cut in the corresponding sidewalls 138, 140. Additionally or alternatively, the handle features 302 may be formed as knobs or other offset structures projecting outward from the corresponding wall 138, 140. The knobs or offsets may be formed in the walls 130, 140 and/or attached thereto as separate parts.

Figure 4A:
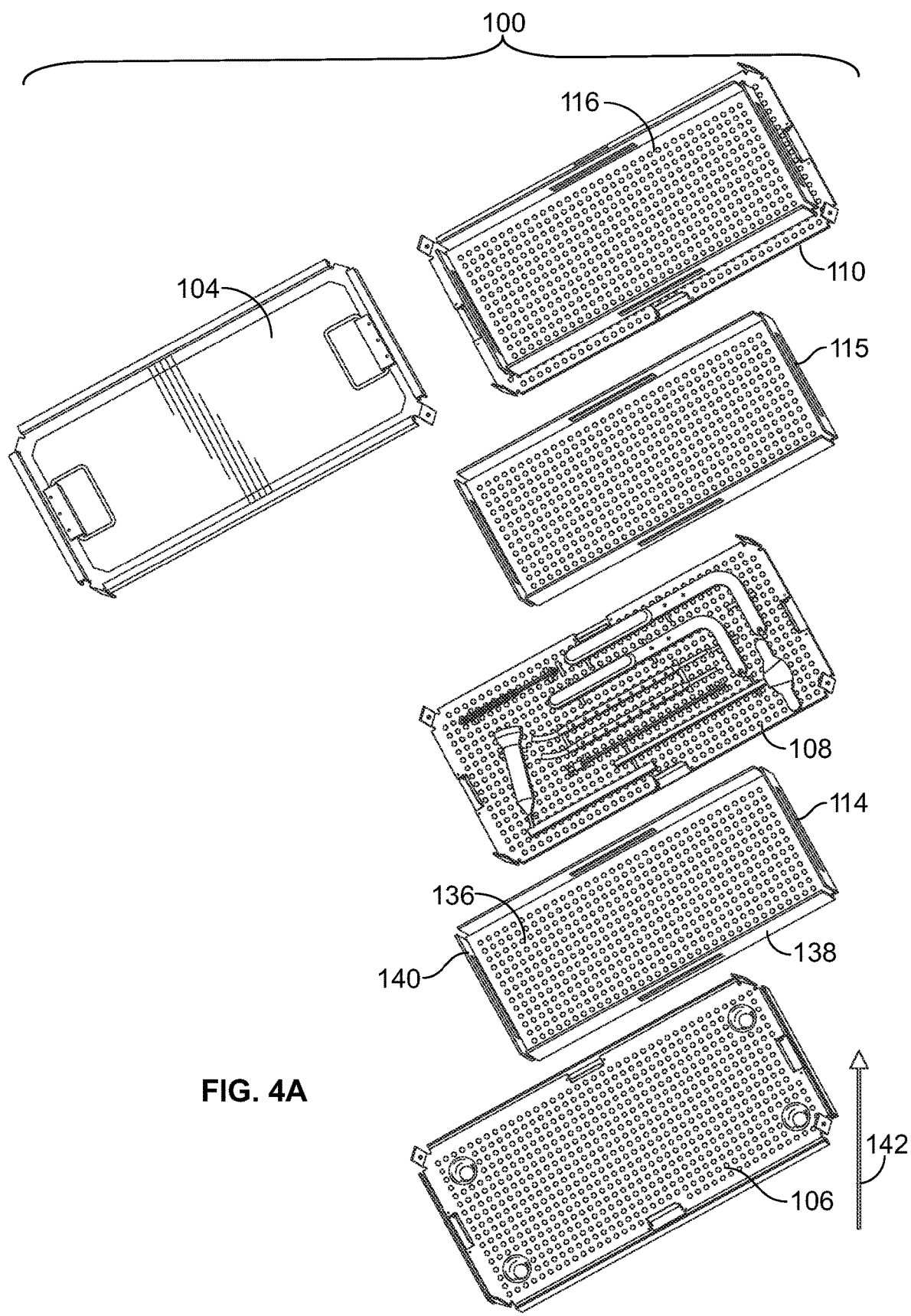
FIG. 4A illustrates the various components of the cabinet in an exploded arrangement.

FIG. 4A illustrates the various component layers of the cabinet 100 in an exploded arrangement. More specifically, FIG. 4A illustrates the top plate 104, bottom shelf 106, shelves 108, 110 and trays 114-116. The upper instrumentation retention tray 116 is shown positioned upon the corresponding shelf 110. Next, the discussion of an individual tray will be described in connection with instrumentation retention tray 114. However, it is recognized that all or at least a portion of the trays may have a similar structure.

The tray 114 includes include a baseplate 136 with walls 138 and 140 surrounding the baseplate 136. In the present example, the walls 138, 140 substantially entirely surround the baseplate 136. Optionally, gaps or notches may be formed in the walls 138, 140 such that the walls 138, 140 do not necessarily form a solid continuous border around the perimeter of the baseplate 136. In the present example, the walls 138, 140 have a common height, however it is recognized that the walls 130, 140 may have different heights or may have uneven heights along individual walls. The baseplate 136 and walls 138, 140 form an instrumentation storage area configured to receive multiple surgical instruments. The walls 138, 140 extent upward from the baseplate 136 to an open upper space representing an open instrumentation access area to afford easy access to the instruments within the instrumentation retention tray 114.

In the present example, the cabinet 100 is formed with two intermediate shelves 108, 110 to provide areas to retain three instrumentation retention trays 114-116. However, it is recognized that embodiments may be formed with a single intermediate shelf 108 to provide areas for two instrumentation retention trays. As another option, more than two intermediate shelves may be provided to form areas for more than three instrumentation retention trays. Also, in the present example, the spacing between the bottom shelf 106, intermediate shelves 108, 110 and top plate 104 is generally the same. However, optionally the spacing between the bottom shelf 106, intermediate shelves 108, 110 and top plate 104 may differ from one another to allow the use of trays having different heights within an individual cabinet 100. For example, the lowest tray storage area, proximate to the bottom shelf 106, may be formed with a greater height as compared to a height of the top tray storage area, proximate to the top plate 104. By providing a taller tray storage area near the bottom of the cabinet 100, embodiments herein allow for the bottom instrumentation retention tray to retain larger and potentially heavier instruments, while the top instrumentation retention tray retains smaller for lighter instruments, thereby providing a better counter-balanced configuration to resist tipping as upper shelves are opened, but not entirely removed.

The bottom shelf 106, shelves 108, 110 and instrumentation retention trays 114-116 are formed with a plurality of holes there through to allow passage of a sterilization medium during a sterilization process. For example, an array of holes may be punched through baseplates in each of the shelves 106, 108, 110 and instrumentation retention trays 114-116. Optionally, holes may be provided in the side walls of the trays and/or doors 120-123. In accordance with some embodiments, the array of holes may follow a common pattern and spacing throughout all of the shelves 106, 108, 110 and instrumentation retention trays 114-116, such that the holes at least partially align with one another in a vertical direction 143. It may be desirable for the holes to align with one another in the vertical direction 143 to facilitate transfer of the sterilization medium (e.g., hot air, hot steam, etc.) upward through the entire housing 102 when the sterilization medium is injected under high pressure through the bottom surface of the bottom shelf 106.

Figure 4B:
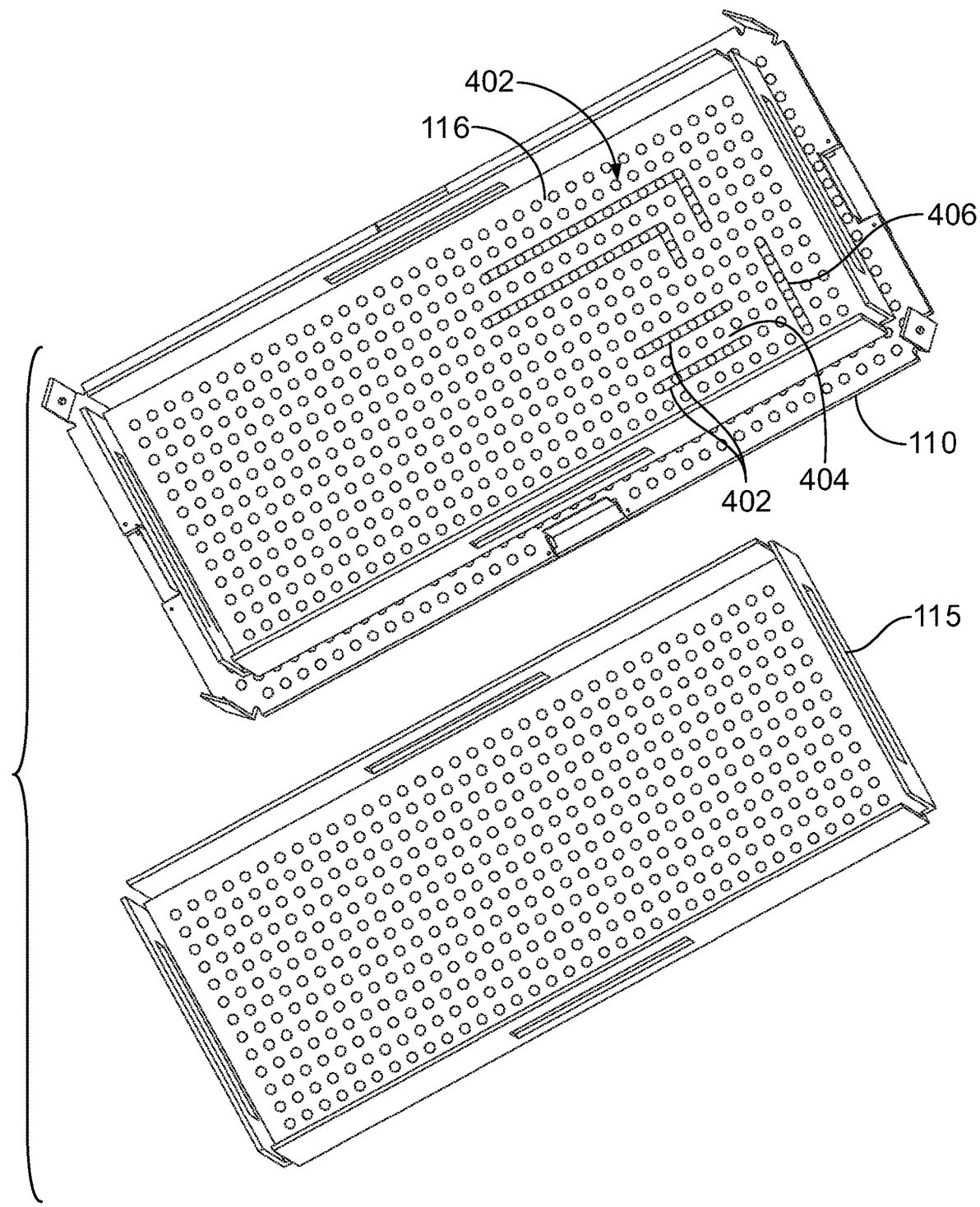
FIG. 4B illustrates instrumentation retention trays with instrumentation alignment features mounted therein in accordance with embodiments herein.

FIG. 4B illustrates instrumentation retention trays with instrumentation alignment features mounted therein in accordance with embodiments herein. For example, the instrumentation retention trays 115, 116 are illustrated to include instrumentation alignment features 402. As one example, the instrumentation alignment features 402 may be mounted to the tray base by friction fitting post through one or more of the holes stamped in the tray bases. As another example, the instrumentation alignment features 402 may be adhesively secured to, or molded with, the tray base. As a further example, the instrumentation alignment features 402 may be formed monolithically within the tray base, such as by stamping or otherwise shaping the tray base to include indentations defining patterns corresponding to specific instruments.

As one example, the instrumentation alignment features 402 may include a pair of opposed ribs 404 that are aligned to extend parallel to one another and are spaced apart to define an instrumentation inset 404 therebetween. Optionally, an end rib 406 may extend perpendicular to or at another select angle with respect to the ribs 404. The end rib 406 is spaced apart from the opposed ribs 404, such that the collection of end and opposed ribs 406, 404 define a generally T-shaped instrumentation inset 404. In the present example, the ribs 404, 406 are mounted to the tray base through posts that are pushed through one or more of the holes in the tray base and held therein in a frictional manner or with snapping features on distal ends of the post once pressed through corresponding holes. It is recognized that numerous combinations of instrumentation alignment features 402 may be provided based on the nature, shape and size of the instruments to be retained within the corresponding instrumentation retention tray 115, 116. The ribs 404, 406 may be removed and reset in various patterns, such as when it is desirable to reconfigure an instrumentation retention tray to receive a different combination of instruments for a subsequent procedure.

Optionally, the instrumentation alignment features may be molded with or stamped into the tray base, wherein such features will similarly have a shape that defines instrumentation insets corresponding to the particular types of tools to be held in the instrumentation retention tray 115, 116. For example, when Radel® material is used, instrumentation insets may be molded directly into the top surface of the tray base, where each instrumentation inset is shaped to correspond to a desired instrument. Further, the use of Radel® material to form the trays allows for a lighter overall tray structure. Optionally, the instrumentation inset 404 may be colored or provided with other indicia that generally indicates an outline of the instrumentation to be received therein. For example, when the instrumentation inset 404 is intended to receive a hammer, a portion of the tray base may be colored with a pattern corresponding to the shape of the hammer and provided in the region intended to receive the hammer.

Figure 5A:
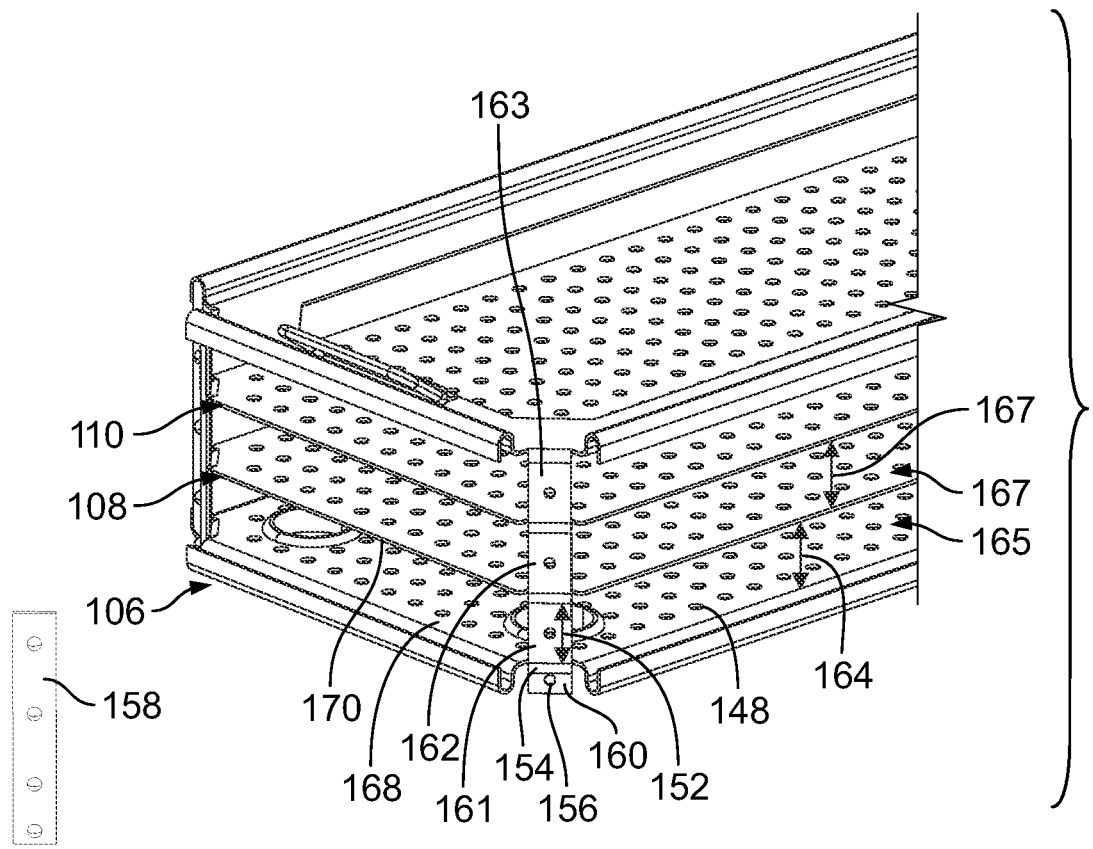
FIG. 5A illustrates an enlarged perspective in view of a corner of the housing formed in accordance with embodiments herein.
Figure 5B:
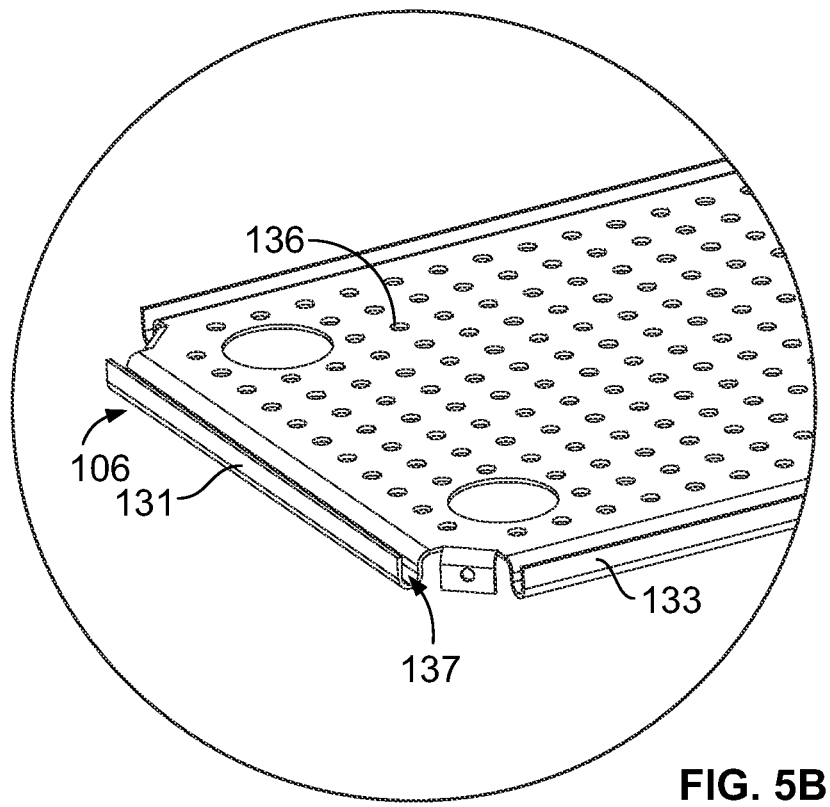
FIG. 5B illustrates an enlarged perspective view of the corner of the bottom shelf.

Next, FIGS. 5A and 5B are discussed in connection with an example embodiment for a standoff to define heights of the tray storage areas. FIG. 5A illustrates an enlarged perspective in view of a corner of the housing 102 formed in accordance with embodiments herein. FIG. 5B illustrates an enlarged perspective view of the corner of the bottom shelf 106. It should be recognized that, while the following discussion may primarily refer to the bottom shelf 106, the top plate 104 and bottom shelf 106 and shelves 108, 110 may include all or a portion of the same features.

FIG. 5A illustrates a corner of the housing 102 with the standoff 112 in a partially disassembled state in accordance with embodiments herein. The top plate 104, bottom shelf 106 and shelves 108, 110 are arranged in an assembled position. A tray storage area 165 is provided between the bottom shelf 106 and the next adjacent shelf 108, while a tray storage area 166 is formed between the adjacent intermediate shelves 108, 110. The bottom shelf 106 includes a baseplate 136 having an upper surface 168 that faces a lower surface 170 of the adjacent intermediate shelf 108. The upper surface 168 of the baseplate 136 is spaced a height 164 from the lower surface 170 of the shelf 108. The height 164 corresponds to a height of the tray storage area 165. Similarly, an upper surface of the shelf 108 is spaced a height 167 from the lower surface of the adjacent shelf 110, where the height 167 corresponds to a height of the tray storage area 166.

In accordance with some embodiments, it may be desirable to maintain a relatively close tolerance between the heights 164, 167, etc. of the tray storage areas and a height of the walls on the instrumentation retention trays to hold the trays stable in an open position/state. For example, a relatively close tolerance may be desirable to avoid instrumentation from inadvertently falling out of a tray when the cabinet is moved (e.g., tipped, turned upside down, laid on a side, etc.) As another example, it may be desirable to maintain a close tolerance between the heights 164, 167 and the wall height in order that the shelfs support the instrumentation retention trays in a substantially horizontal orientation even when the instrumentation retention trays are opened to a fully open position/state. More generally, the close tolerance between the heights 164, 167 and the wall height maintains the instrumentation retention trays aligned along planes that correspond to associated planes of the supporting shelves. As noted herein, feet may be provided on the bottom surface of the trays, in which case, the height of the tray would extend from the bottom of the feet to the top of the highest point, such as the top edge of the side and end walls.

The heights of the tray storage areas 165, 166, etc. are defined by the standoff 112. The standoff 112 may be formed from two parts, namely a bracket connector 158 and a series of tabs 160-163 that align and directly stack upon on one another when the top plate 104, bottom shelf 106 and shelves 108, 110 are arranged in an assembled position. The tab 161 is formed with the baseplate 136 and is located proximate to a corner of the baseplate and is bent downward to extend outward in a direction transverse from a plane of the baseplate. By way of example, the tab 161 may be bent to form an approximate 90° angle with respect to the surface of the baseplate. Optionally, the tab 161 may be bent to extend at an obtuse or acute angle to the baseplate. Similarly, the tabs 160 and 162 may be formed in a similar manner and bent to extend in a desired direction transverse to the corresponding shelf or top plate 104 such that the tabs 160-163 align with, directly about against and stack upon one another. Optionally, the all or a portion of the tabs 160-163 may be bent upward to extend in a direction opposite to the direction illustrates. Optionally, a portion of the tabs 160-163 may be bent upward, while another portion of the tabs 160-163 are bent downward.

The tab 161 has a height 152 that may be utilized to define the height 164 of the tray storage area 166. For example, the tab 161 may include an engagement surface that directly engages a corresponding engagement surface on tab 160 at interface 154. An engagement surface of the tab 162 directly engages a corresponding engagement surface on tab 161 to define the height 167 of the tray storage area 166. The tabs 160-163 are shown to include holes 156 that align with holes in the bracket connector 158 when the bracket connector 158 is mounted to the tabs 160-163. The bracket connector 158 is secured to the tabs 160-163, such as through bolts, rivets, welds and the like.

Optionally, one or more combinations of the adjacent tabs 160-163 may be spaced apart from one another when secured to the bracket connector 158. For example, the bottom and intermediate shelves 106, 108 may be spaced further apart by separating the tabs 160, 161 and securing the tabs 160, 161 to a combination of holes through the bracket connector 158 that are spaced apart. In the foregoing manner, the bracket connector 158 affords flexibility to adjust heights of individual tray storage areas. Optionally, the height of tray storage areas may be adjusted by adjusting the length of the corresponding tab 160-163.

Optionally, the bracket connector 158 may be removed entirely and the tabs 160-163 joined in other manners, such as adhesive, welding and the like to form the standoff 112. Optionally, the tabs 160-163 may be omitted entirely and the bracket connect 158 may be used to hold adjacent shelfs apart from one another by a desired distance. Optionally, additional components may be included in addition to or in place of the bracket connector 158 and/or the tabs 160-163. For example, a spacer (e.g., straight, U-shaped, C-shaped etc.) may be inserted between adjacent shelfs at desired points to define the distance between adjacent shelfs. It is recognized that any portion of the foregoing examples constitute standoffs, as well as other alternative structures.

It should be recognized that portions of the intermediate shelves 108, 110 have been removed to better illustrate the above discussed features in connection with FIG. 5A. The intermediate shelves 108, 110 also include side walls and end walls 138, 140 as discussed herein.

FIG. 5B better illustrates a corner segment of the bottom shelf 106 in accordance with embodiments herein. As explained above, the bottom shelf 106 includes a baseplate 136 that is a generally planar layer of material. The baseplate 136 includes an array of holes 148 punched there through in a pattern that substantially conforms to the array of holes in the other shelfs and instrumentation retention trays in the cabinet 100. The bottom shelf 106 includes a rail 131 extending along a longitudinal edge thereof and a rail 133 extending along a transverse edge thereof. The rails 131, 133 may be formed with the baseplate 136, such as through a stamp informing operation, as well as through other known machining processes. The rail 131 includes a groove 137 having an open end that is configured to slidably receive a corresponding door, such as the side door 120 (FIG. 1A).

Figure 5D:
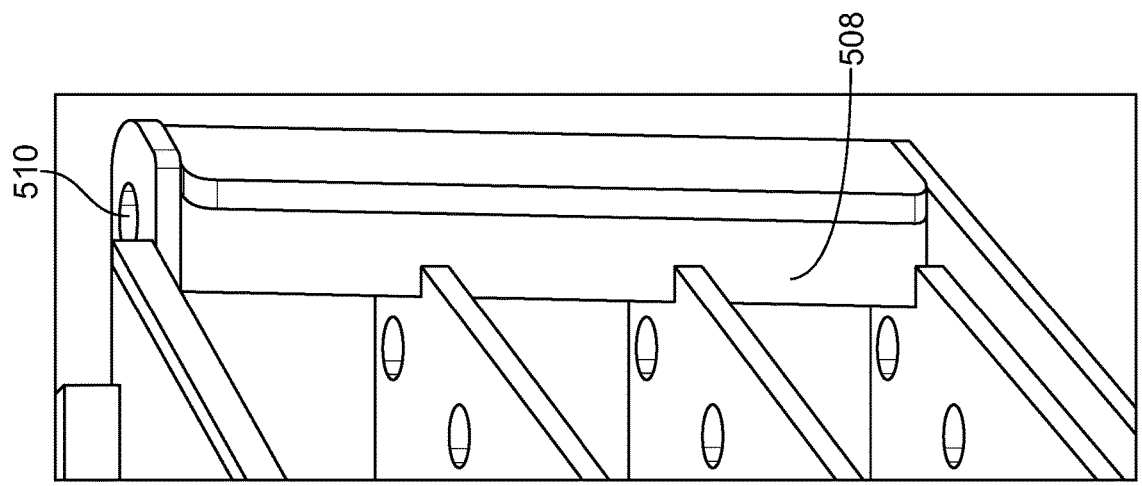
FIG. 5D illustrates a rear perspective view of a corner connector formed in accordance with an alternative embodiment.
Figure 5C:
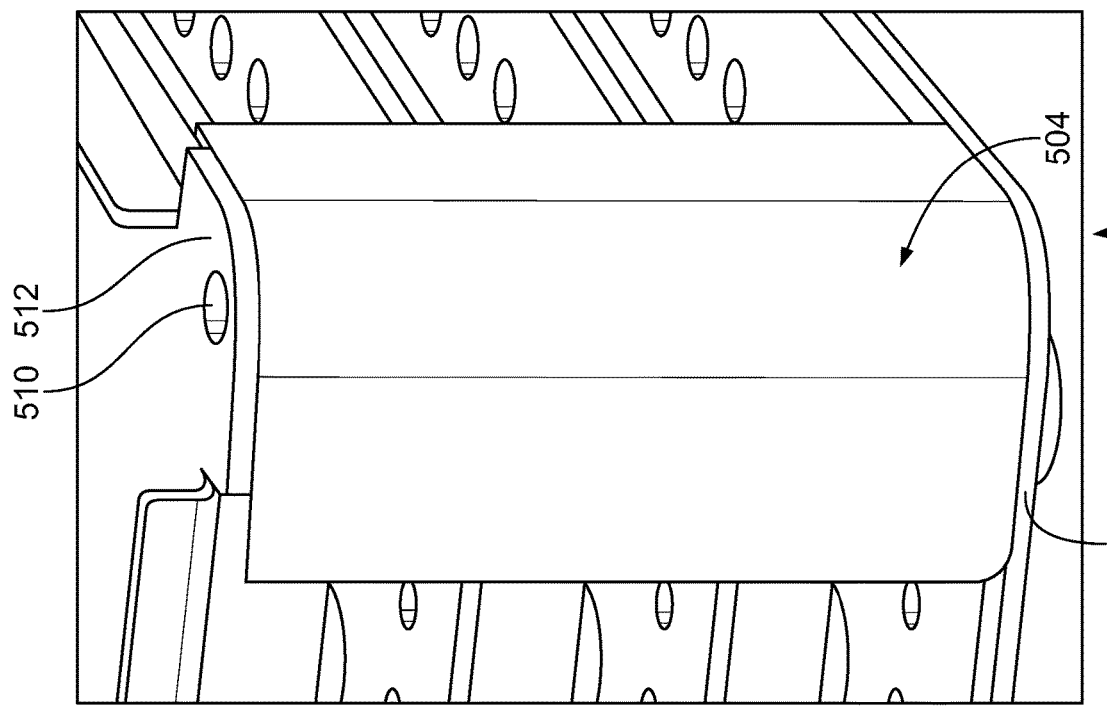
FIG. 5C illustrates a front perspective view of a corner connector formed in accordance with an alternative embodiment.

FIGS. 5C and 5D illustrate front and rear perspective views of a corner connector formed in accordance with an alternative embodiment. The corner connector 502 includes a curved bracket 504 is bent at approximately a 90° angle. The bracket 504 sits on a corner portion of the bottom shelf at 506, while a corner portion of the top shelf is held within the bracket 502. The bracket 502 further includes a shelf spacer 508 having a next to rear surfers that is curved to fit against an interior surface of the bracket 504. The shelf spacer 508 may be formed as multiple separate spacers that are fit between the shelves, were the heights of the spacers define the height between adjacent shells. Alternatively, the shelf spacer 508 may be formed as one continuous monolithic piece with a series of notches formed therein, or the notches are configured to receive corner portions of corresponding shelves. The spacing between the notches defines the height between adjacent shells. A securing mechanism 510, such as a screw may be threaded down through the bracket to secure the shelves to the corner connector 502. For example, a threaded bolt or screw may be fitted through aligned holes within the shelf spacer 508 and corresponding holes in corner portions of each of the shelves. A top plate 512 may be pressed downward by the securing mechanism 510 to compress down upon the corner portion of the top shelf. Optionally, the top plate 512 may be omitted and the corner portion of the top shelf used in place thereof.

The embodiment of FIGS. 5A and 5B may provide a more efficient design that reduces the overall envelope of the corner portion, thereby allowing the instrumentation retention trays to be made larger, and have a size only slightly smaller than the overall envelope of the cabinet.

Figure 6:
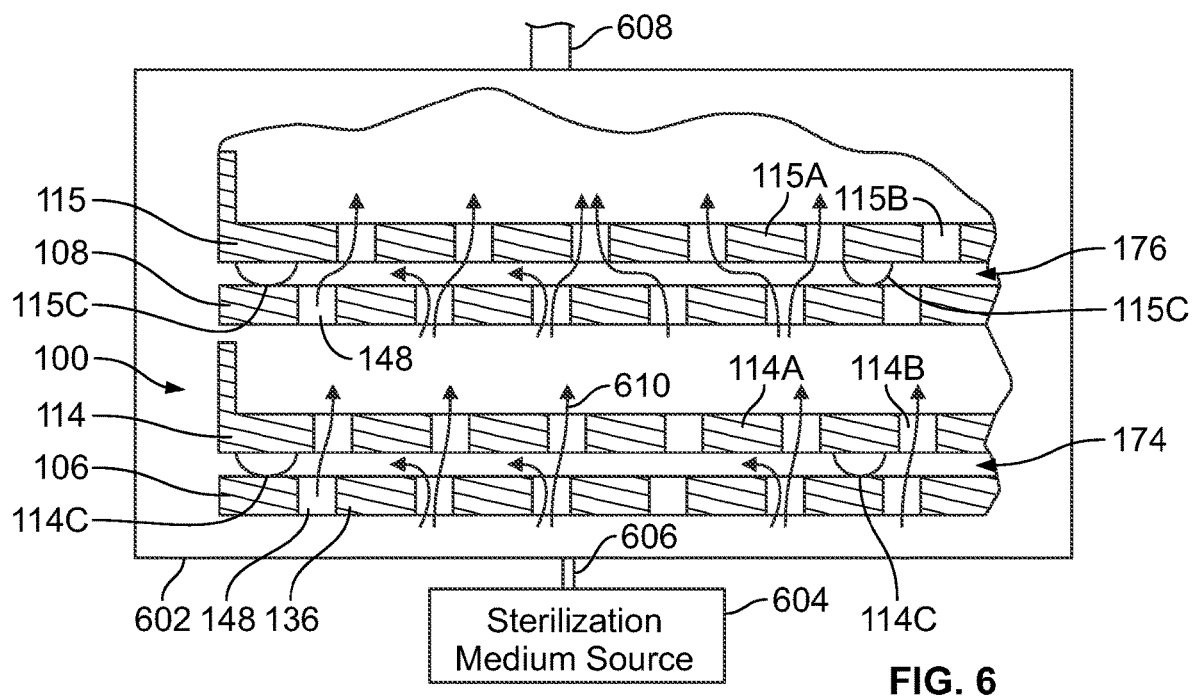
FIG. 6 illustrates a portion of the cabinet while loaded into a chamber configured to perform a sterilization process.

FIG. 6 illustrates a portion of the cabinet 100 while loaded into a chamber 602 configured to perform a sterilization process. The illustrated portion of the cabinet 100 may include a portion of the bottom shelf 106, tray 114, intermediate shelf 108 and tray 115. The trays 114 and 115 rest upon the corresponding bottom and intermediate shelves 106, 108. FIG. 6 illustrates a portion of the baseplate 136 of the bottom shelf 106, including a portion of the array of holes 148 through the baseplate 136. The trays 114-115 include tray baseplates 114A and 115A, respectively, that include an array of holes 114B and 115B there through. As shown in FIG. 6, the holes 114B and the tray baseplate 114A at least partially align with the holes 148 in the baseplate 136 of the bottom shelf 106. The holes 115B in the tray baseplate 115A of the intermediate tray 115 do not overlap with the holes 148 in the intermediate shelf 108.

Bottom surfaces of the trays 114, 115 include feet 114C and 115C, respectively. The feet 114C, 115C may be formed in various manners, such as molded into or mechanically attached to the underside of the trays 114, 115. The feet 114C, 115C may be located in various locations on the trays 114, 115 to allow the trays 114, 115 to rise off the shelves and create a space therebetween. For example, the feet 114C, 115C may be formed from the tray baseplates 114A, 115A such as by pressing indents or dimples in the tray baseplates 114A, 115A. Optionally, the feet 114C, 115C may represent screws, tabs or other structures that are attached to the bottom surface of the corresponding tray 114, 115 and the like. Optionally, feet 114C, 115C may be formed in or provided on the upper surface of the baseplates of the shelves 106, 108. The feet 114C, 115C are configured to maintain a space between the trays 114, 115 and shelves 106, 108 in order to define air passages 174 and 176. The feet 114C on the tray 114 maintain the air passages 174 between a bottom surface of the tray baseplate 114A and an upper surface of the bottom shelf 106. The feet 115C maintain the air passages 176 between a bottom surface of the tray 115 and an upper surface of the intermediate shelf 108. The air passage 174, 176 facilitates the sterilization process, as well as a space for the underside of the instrumentation brackets to extend though the tray base. The air passages 174, 176 enable a sterilization medium to pass through the holes 148, 114B and 115B, as well as to pass along and substantially encompass each and every surface of the bottom and intermediate shelves 106, 108 as well as each and every surface of the trays 114, 115. In addition, the air passages 174, 176 enable the surfaces of the shelves 106, 108 and trays 114, 115 to dry after completion of a sterilization process to avoid "wet pack".

Optionally, the feet 114C, 115C may be formed form silicon to provide some grip or tension between the tray 114, 115 and the shelves for more control when pulling out the trays 114, 115 partially. The feet 114C, 115C also serve the purpose of keeping the trays from being too loose while housed in the shelving. The feet may be provided at the corners of the tray base and/or distributed through out the tray base, such as to avoid the outer edge of the tray from dropping when initially pulled out by an amount sufficient for the first two feet to clear the shelf.

Additionally or alternatively, instrumentation retention brackets may be attached to the baseplates 114A, 115A of the trays 114, 115, wherein the instrumentation retention brackets are configured to retain instrumentation within a corresponding tray. The instrumentation retention brackets may be inserted through the holes 148 to be secured to the baseplates 114A, 115A. Additionally or alternatively, the instrumentation retention brackets may be inserted through additional slots or separate openings formed through the baseplates of the trays to secure the instrumentation retention brackets in place. The distal portions of the instrumentation retention brackets that extend through the baseplate 114A, 115A, may be used in addition to or in place of the feet 114C, 115C to define the air passages 174, 176.

A sterilization medium source 604 provides a sterilization medium to the chamber 602. Various types of medium may be used during the sterilization process, such as heated air, steam, liquid or vapor chemicals and the like. The sterilization medium travels through the chamber 602 in a predetermined direction and/or multiple random directions. For example, the chamber may include an inlet 606 through which the sterilization medium is introduced and one or more outlets 608 through which the sterilization medium is discharged. For example, heated and pressurized error or steam may be passed through one or more inlet 606 and discharged from one or more outlets 608. The sterilization medium propagates through any and all interior passages within the cabinet 100 in order to sterilize all surfaces of the cabinet 100. In FIG. 6, a series of paths are denoted by arrows 610 to illustrate the manner in which the sterilization medium is allowed to touch substantially every upper and lower surface of the shelves 106, 108 and trays 114, 115, as well as all other layered components and structures of the cabinet 100.

While the pattern of holes 148, 114B and 115B are illustrated to be substantially similar to one another, optionally, different hole patterns may be provided in different shelves 106, 108 and/or different trays 114, 115. The alignment between the holes 148 in the shelves 106, 108 and the holes 114B, 115B may vary as the trays 114, 115 may laterally shift in the longitudinal and transverse directions (e.g. 124, 144 in FIG. 1A) relative to the shelves 106, 108 while maintained in a storage position.

Optionally, the cabinet may be inserted and stored into a closed rigid outer container (e.g., an Asculap container). Optionally, the cabinet may be wrapped in disposable, single-use wrap (e.g., Chemguard wrap, sterilization wrap products by Medline or other companies).

Figure 7:
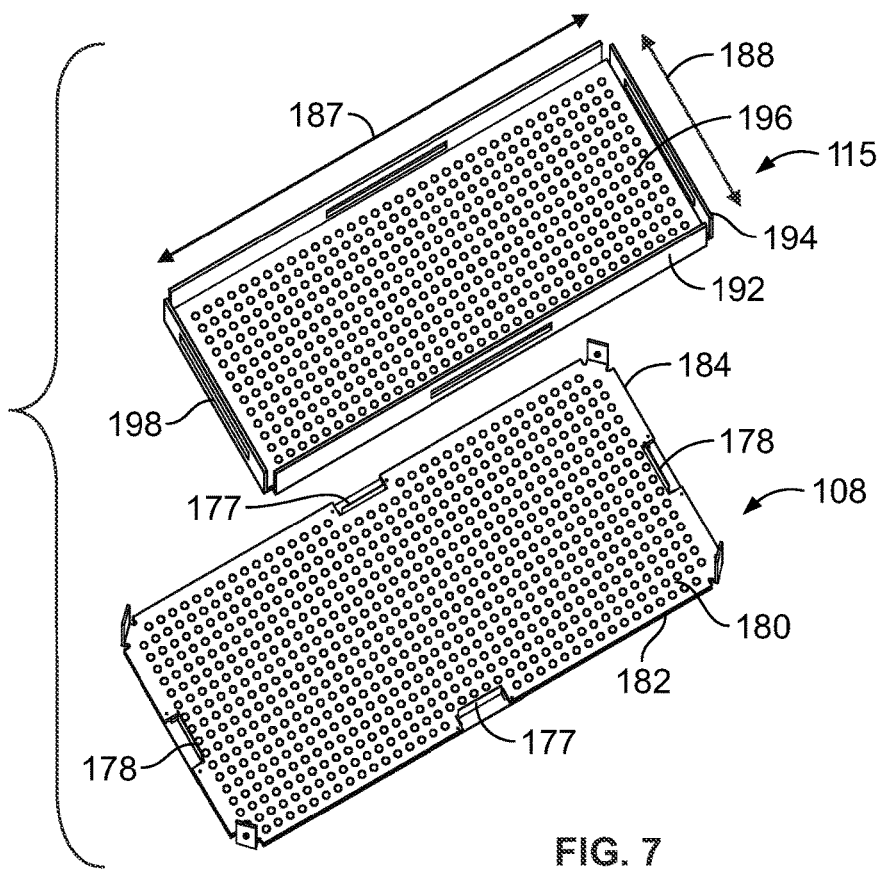
FIG. 7 illustrates a side perspective view of an intermediate shelf and a tray configured to cooperate with one another.

FIG. 7 illustrates a side perspective view of an intermediate shelf 108 and a tray 115 configured to cooperate with one another. The tray 115 has sidewalls 192 and end walls 194 that extend upward from the tray base 196 to define an instrumentation storage area there between. For example, the side and end walls 192, 194 may be formed with the tray base 196 and bent in a desired direction to form the instrumentation storage area. Additionally or alternatively, one or more of the sidewalls and end walls 192, 194 may be formed separately and assembled with the tray base 196. One or more of the side and end walls 192, 194 may include gripping elements 198 that enable a user to easily grasp of the tray 115 when the tray is in a tray storage position within the cabinet 100. The gripping elements 198 may be formed as indents pressed into the corresponding side or end walls 192, 194. Optionally, the gripping elements 198 may be mounted to the side or end walls 192, 194. The tray 115 may have a length 187 and a width 188.

In the example of FIG. 7, the sidewalls 192 and end walls 194 generally intersect at an approximately square corner. Optionally, the tray 115 (and any/all other trays) may be formed with beveled corners.

The shelf 108 includes a baseplate 180 that has tray retention fins 177, 178 that extend upward therefrom. The tray retention fins 177 and 178 are positioned proximate to side edges 182 and end edges 184, respectively, of the baseplate 180. The tray retention fins 177 and 178 define a length and width of a tray storage area, and cooperate to maintain the tray 115 in a relatively fixed position when in the tray storage area. The tray retention fins 178 proximate to the end edges 184 are spaced apart from one another at opposite ends by a distance substantially similar to a longitudinal length 187 of the tray 115. The tray retention fins 177 proximate to the side edges 182 are spaced apart from one another at opposite sides by a distance substantially similar to a width 188 of the tray 115. The tray retention fins 177, 178 prevent the tray 115 from inadvertently slighting out of a tray storage area.

To remove the tray 115 from the corresponding tray storage area, a user grasp a side or end of the tray (depending upon the direction in which the user desires to pull out the tray). The user lifts up slightly to raise the end or side of the tray 115 up and over the corresponding tray retention fin 177, 178, while pulling outward (and/or pushing on an opposite end/side) of the tray 115 until the leading edge of the tray 115 crossed over the corresponding tray retention fins 177, 178. Thereafter, as the tray 115 is further slid from the tray storage area, a bottom surface of the tray 115 slides along the top of the corresponding fin 177, 178.

Figure 8:
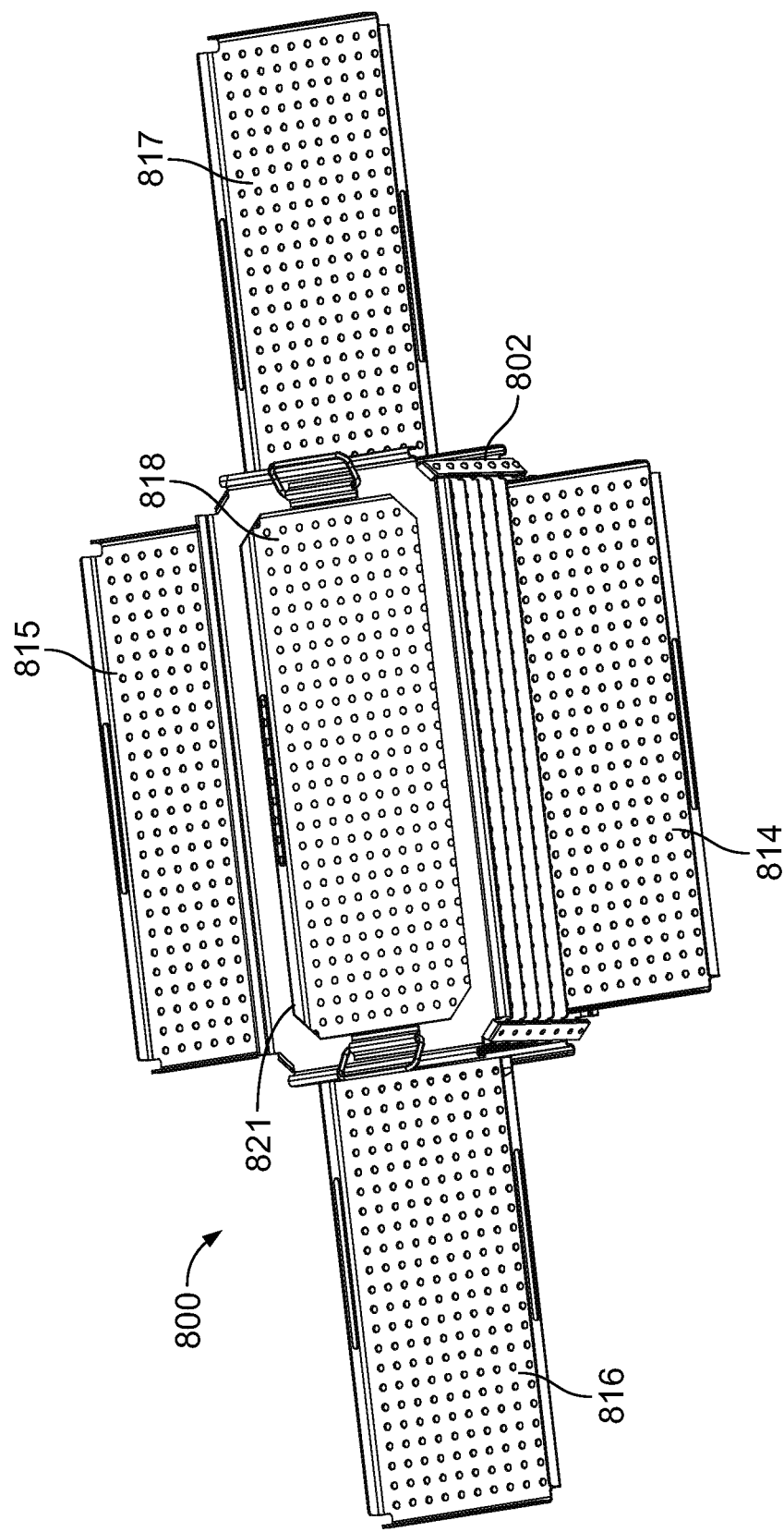
FIG. 8 illustrates a top front perspective view of a cabinet with a housing that includes more than two intermediate shelves.

FIG. 8 illustrates a top front perspective view of a cabinet 800 with a housing 802 that includes more than two intermediate shelves. The cabinet 800 holds at least five trays 814-818, with trays 814-815 opened from the front and back sides and the trays 816-817 opened from the ends. A top plate 804 is formed with an opening 821 therein. The opening 821 may be covered with a clear material to allow content of the tray to be visible. Optionally, the opening 821 may be closed and opened with a lid (solid or transparent).

Figure 9A:
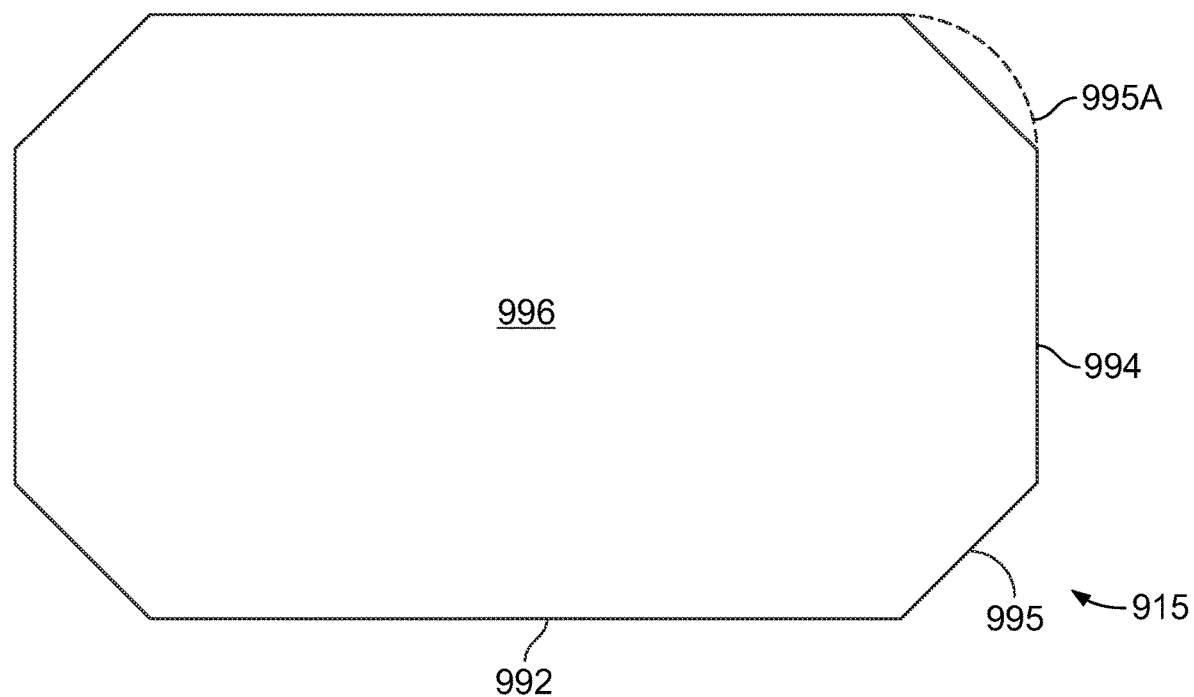
FIG. 9A illustrates a top plan view of a tray formed in accordance with an embodiment herein.

FIG. 9A illustrates a top plan view of a tray 915 formed in accordance with an embodiment herein. The tray 915 includes a tray base 996 that is joined to sidewalls 992 and end walls 994 (that project out of the sheet). The tray base 996 is formed with straight beveled corners 995 to avoid the corners catching as the trays are lid in and out in the various directions. As one non-limiting example, the beveled corners 995 may be beveled at an angle between 5-15 degrees. Optionally, the corners 995 may have vertical walls bent upward similar to the sidewalls 192 and/or end walls 194. Optionally, instead of straight edges, the beveled corners 995 may be rounded to form a radius or chamfer bevel (as noted by dashed line 995A) that transitions between the side and end walls 992, 994. Optionally, the beveled corners 995 may be formed with a series of straight angles, such as along an edge of a hexagon, octagon or other multi-sided polygon.

Next, the discussion turns to an alternative configuration for the top plate (e.g. top plate 104) and a manner in which the top plate is pivotally and removably attached to the cabinet.

Figure 9B:
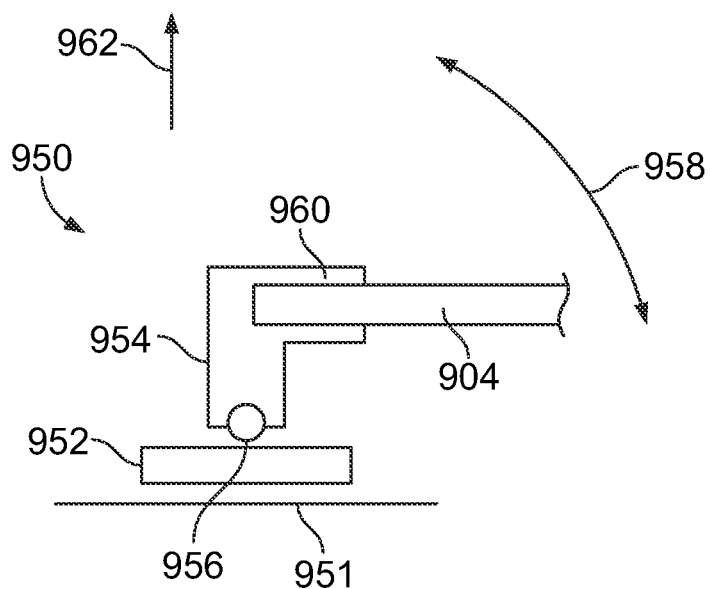
FIG. 9B illustrates an end view of a top plate hinge assembly that may be mounted on a top of a cabinet housing in accordance with embodiments herein.
Figure 9C:
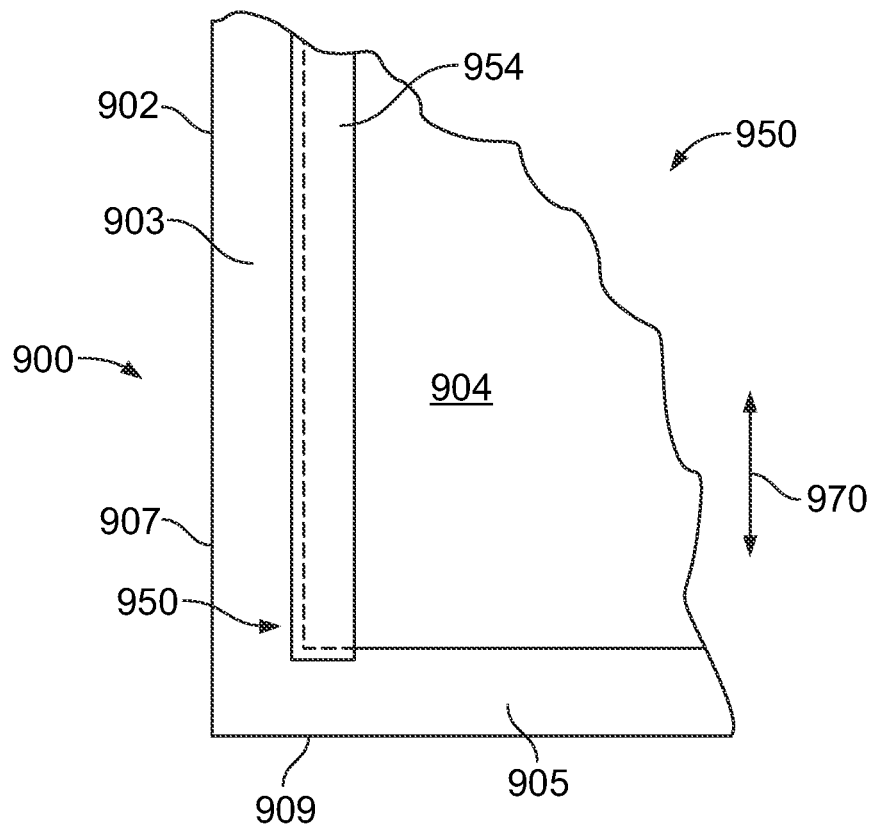
FIG. 9C illustrates a top plan view of the top plate hinge assembly of FIG. 9B, when mounted to a housing of a cabinet in accordance with embodiments herein.

FIG. 9B illustrates an end view of a top plate hinge assembly 950 that may be mounted on a top of a cabinet housing in accordance with embodiments herein. The hinge assembly 950 includes a base 952 configured to be mounted on a top of the housing of the cabinet (e.g. at 951). The hinge assembly 950 further includes a stem 954 pivotally mounted to the base 952, such as at hinge 956. The hinge 956 allows the stem 954 to rotate in the directions noted by arrow 958. The stem 954 includes a top plate retention cavity 960 that is configured to receive an edge of a top plate 904. The retention cavity 960 securely retains the top plate 904, such that as the stem 956 rotates about arrow 958, the top plate 904 similarly rotates in the direction of arrow 958 between a closed position (as illustrated in FIG. 9C) and an open position. By way of example, when the top plate is in the open position, the top plate 904 may be extending vertically upward in an air direction of arrow 962. The hinge 956 may be biased to maintain the top plate 904 in a select number of positions, such as in a horizontal closed position (e.g. as illustrated in FIG. 9B), in a vertical fully open position (e.g. when the top plate 904 is oriented to extend in the direction of arrow 962) and any intermediate point there between. Optionally, the hinge 956 may allow the top plate 904 two pivot beyond a vertical position (e.g. beyond 90° from the position illustrated in FIG. 9B). The hinge 956 may be configured to maintain the top plate 904 at discrete orientations with respect to the horizontal top surface of the housing (951), in order that a medical personnel need merely partially lift the top plate, in response to which the top plate 904 will move upward to the predetermined discrete angle with respect to horizontal (e.g. 45°, 90°, 135°, 180°). Optionally, the hinge 956 may be configured to maintain the top plate 904 at any position along a 180° arc, such that the user merely need lift the top plate 904 two any desired position. When the user releases the top plate 904, the hinge 956 will maintain the top plate 904 at the position where released.

FIG. 9C illustrates a top plan view of the top plate hinge assembly of FIG. 9B, when mounted to a housing of a cabinet in accordance with embodiments herein. The cabinet 900 includes a housing 902 that has a rear side 907 and an end 909. The top of the housing 902 includes a peripheral edge 903, 905 that extends about the rear side 907 and the end 909. The hinge assembly 950 is mounted along the peripheral edge 903, but optionally may be mounted along the peripheral edge 905. FIG. 9C illustrates the top plate 904 and a closed position against the peripheral edges 903, 905 of the housing of the cabinet. The hinge assembly 950 allows the top plate 904 to be rotated upward out of the page in FIG. 9C. The top plate 104 may be removable from the hinge assembly 950. For example, the top plate 904 may be slid in the direction of arrow 972 remove the top plate 904 from either end of the retention cavity 960 (FIG. 9B) in the stem 954. For example, during a procedure, the top plate 904 may remain closed until a corresponding stage of the procedure in which instrumentation within the retention tray immediately below the top plate 904 is needed. When the instruments in the retention tray below the top plate 904 are needed, the top plate 904 may be pivoted upward (along arrow 958) to expose an open top in the housing and to provide access to the upper instrument retention tray. Additionally or alternatively, the top plate 904 may be slid along arrow 972 to be removed from either end of the stem 954 and retention cavity 960.

Figure 10:
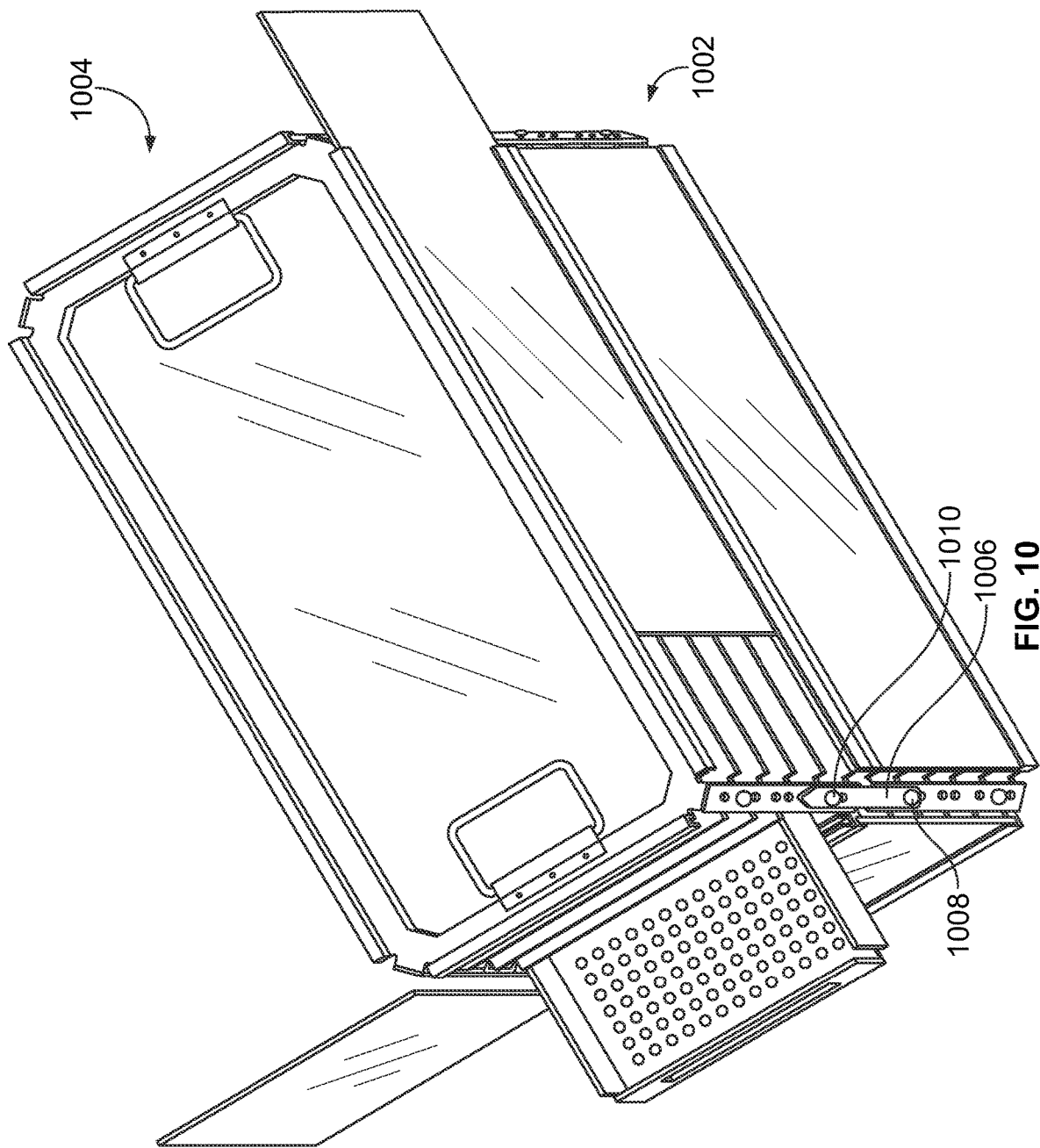
FIG. 10 illustrates a corner perspective view of a pair of cabinets nested with one another in accordance with an embodiment herein.
Figure 10A:
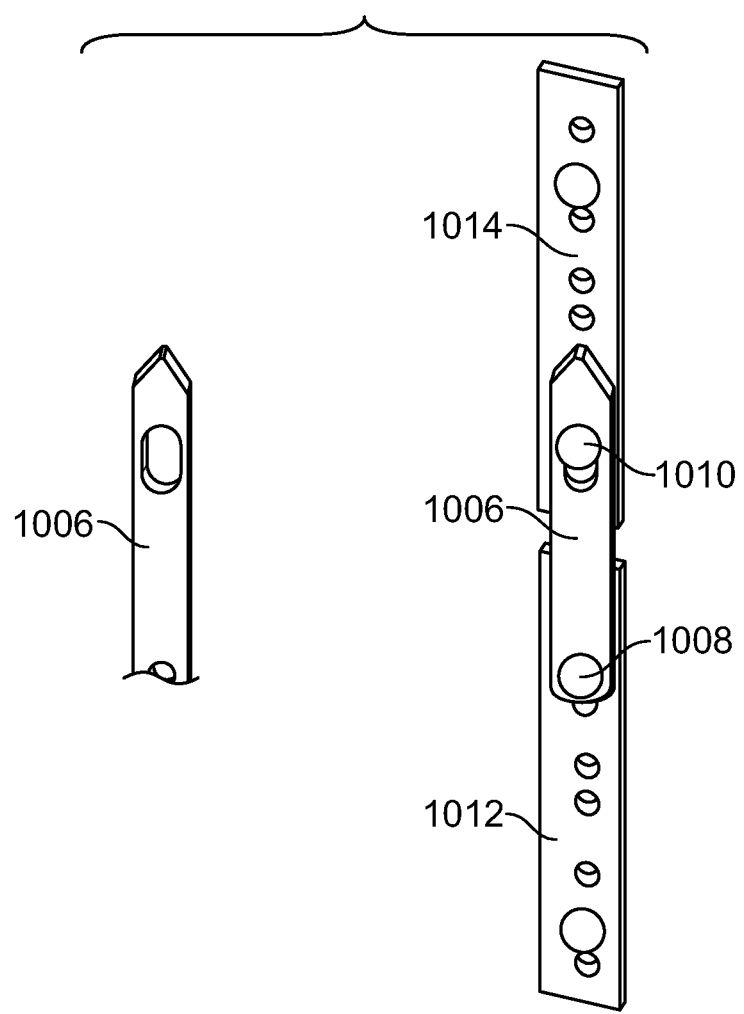
FIG. 10A illustrates a cabinet linking member secured to post provided on respective brackets in accordance with embodiments herein.

FIG. 10 illustrates a corner perspective view of a pair of cabinets nested with one another in accordance with an embodiment herein. FIG. 10 illustrates first and second cabinets 1002, 1004 there stacked upon one another in a nested vertical manner. Each of the cabinets 1002, 1004 include multiple shelves and trays in various combinations as described herein. The cabinets 1002, 1004 are joined together by a cabinet linking member 1006. For example, the cabinet linking member 1006 may be a flexible strap, such as a silicon strap having holes therethrough that may be secured over posts (e.g. post 1008, 1010) provided along the corner brackets of the corresponding cabinets 1002, 1004. FIG. 10A illustrates a cabinet linking member 1006 secured to post 1008, 1010 provided on respective brackets 1012, 1014. The cabinet linking member 1006 is elastic, thereby maintaining a continuous tension pulling the upper cabinet 1004 downward onto the lower cabinet 1002. In the present example, a cabinet linking member 1006 is provided at each corner to secure all four corners of the cabinets 1002, 1004 to one another. Optionally, the cabinet linking members 1006 may be provided in alternative positions and in alternative amounts. For example, more than one cabinet linking member may be provided at any individual corner, while one or more of the corners made not include any cabinet linking members. Optionally, the cabinet linking members may be formed of another material, other than a silicon strap.

As a further example, the straps may be formed through molding or a diecut and made of a medical grade silicone that would attach to flanged protrusions extending from the top and/or bottom of the corner connectors. The protrusions could be formed as a hook or button that is formed or molded into the corner connector. Optionally, the protrusion could represent a screw or other part that is attached to the corner connector. The strap is manually stretched over the hooks, buttons or other protrusions located near the bottom of one corner connector and the top of another corner connector. Optionally, the straps could have sufficient strength to enable a group of cabinets to be picked up and moved in combination by simply hanging onto the handles on the top cabinet.

Optionally, in accordance with embodiments herein, one or more cabinets may be provided with trays containing instrumentation organized in connection with particular procedures. For example, a procedure may represent a thoracolumbar, cervical or interbody anterior or posterior open or minimal invasive spinal fusion procedure. For example, the first tray may correspond to a screw preparation tray. As one example, the screw preparation tray may include gear shifts, taps, sounders, screwdrivers, handles, screw gauges, and the like. As another example, the second tray may correspond to a rod manipulation/insertion tray, which may include benders, screwdrivers, counter torques, rod grippers, rod pushers, rods, rod reducers and the like. The third tray may correspond to a miscellaneous instrumentation tray or an implant tray housing the desired surgical screws corresponding to the particular type of procedure. It is recognized that the foregoing example is only one non-limiting example. Other non-limiting examples of procedures include cervical procedures and the like.

As non-limiting examples, many types of surgeries can be organized into stages of surgery. Optionally, a surgery may be organized into two stages, three stages, four stages or more stages. One type of pediatric surgery is an AIS (Adolescent Idiopathic Scoliosis). For example, an AIS surgery may operate on various vertebrae, such as the T3-L3 vertebrae, with the T3 representing the $3^{rd}$ vertebrae in the thoracic spine and spanning Down to L3 which is the $3^{rd}$ vertebrae in the Lumbar spine etc. As another example, the surgical procedure may involve an Adult Posterior Spinal Fusion, for which example levels range from T10-sacrum and pelvis or even larger cases that are instrumented T2-sacrum and pelvis. Another example of a surgical procedure would be a degenerative lumbar procedure which would not span as many levels as mentioned previously, but instead the degenerative lumbar procedure focuses on fewer levels such as a L2/3-L5 or a L2-sacrum and pelvis instrumented posterior fusion. Obviously there are many type of procedures. Also, the procedures may approach the spine in different manners, such as anterior and posterior cervical fusions and anterior, posterior, MIS (Minimal Invasive Surgery), or a combination of these approaches for a variety of surgeries etc. The foregoing are non-limiting examples of procedures. Embodiments herein may be utilized with many different specialties in addition to spine including ENT, cardio thoracic, plastic, eye etc. and offers many potential benefits to include, but not limited to, time savings, cost savings, safety, flexibility, and potential contamination benefits.

An overall procedure may utilize an overall procedure set of instruments. The surgical procedure may be separated into 2, 3 or more stages. Each stage of the surgical procedure utilizes a subset or collection of instruments from the overall set of instruments. Some or all of the instruments in a predetermined subset or collection of instruments may be used during a corresponding stage. The collection of instruments that may be utilized in a particular stage of a procedure may also be referred to herein as stage-specific instruments (e.g., stage-1 instruments, stage-2 instruments, exposure stage instruments, rod manipulation stage instruments, and the like). More generally, a procedure may be divided into first, second, and third stages (and optionally more stages). The overall procedure set of instruments that is divided into first, second and third (and optionally more) subsets or collections of instruments are configured to be used in the corresponding first, second and third stages of the procedure. The first subset or collection of instruments is configured to be utilized in connection with particular tasks or actions taken during the first stage. The second subset or collection of instruments is configured to be utilized in connection with particular tasks or actions taken during the second stage. The third subset or collection of instruments is configured to be utilized in connection with particular tasks or actions taken during the third stage.

In accordance with embodiments herein, sets of cabinets may be organized and combined in connection with specific surgical procedures, where one or more cabinets from the set of cabinets may be assigned or dedicated to each stage of the surgical procedure. For example, a first cabinet may be assigned to a first stage, while second and third cabinets are assigned to second and third stages, respectively. Additionally or alternatively, a subset of two or more cabinets may be assigned to one of the stages, while a same number of cabinets, fewer or more cabinets may be assigned to other stages. For example, a subset of two or more cabinets may be assigned to the first stage, a single second cabinet may be assigned to the second stage, two or more cabinets may be assigned to the third stage, and a single fourth cabinet may be assigned to the fourth stage. When a cabinet is described to be "assigned" or "dedicated" to a stage, the cabinet includes only instruments to be used in the corresponding stage. By way of example, the instruments in a rod manipulation stage cabinet are only to be used in the rod manipulation stage of the procedure and are not to be used in the exposure stage or screw insertion stage.

For example, a spine surgery may be broken into three main stages, namely i) exposure stage, ii) screw insertion stage and iii) rod manipulation and closure stage. The exposure stage includes a series of "set up" tasks, which include the tasks performed and time spent by medical personnel in an O.R. room prior to a patient entering the room. Among other things, one of the tasks performed during the set up process is for medical personnel to bring the cabinets and surgical trays into the O.R. and position and arrange the cabinets on various tables and other supports in a desired arrangement about the O.R. in connection with preparing for the procedure. The set up tasks take a set up time to be performed. While different types of surgeries have different set up tasks and set up times, in generally most procedures will require a set up time of at least 30 minutes, and more generally 30-45 minutes.

The exposure stage also includes a series of "patient preparation" tasks, which include bring a patient into the O.R., moving the patient onto an O.R. table, and performing final preparation of the patient for the surgical procedure. The preparation tasks take a preparation time to be performed. While different types of surgeries have different patient preparation tasks and preparation times, in generally most procedures will require a preparation time of at least 20 minutes, and more generally 20-30 minutes.

In accordance with embodiments herein, the instruments in the cabinets remains enclosed and sheltered within corresponding trays and cabinets for an entirety of the setup and preparation tasks, which may range from 50 minutes, to 50-75 minutes or more.

Next, the exposure stage includes a series of exposure tasks to expose a portion of interest for the surgical procedure. The exposure tasks take an exposure time to be performed which can take over 30 minutes and more generally anywhere from 30-60 minutes. In accordance with embodiments herein, the instrumentation in the cabinets, that is unrelated to exposure tasks, remains enclosed and sheltered within corresponding trays and cabinets for an entirety of, not only the setup and preparation stages of the surgical procedure, but also the exposure stage, thereby maintaining the non-exposure related instrumentation (e.g., screw insertion instrumentation and rod manipulation instrumentation) in an enclosed and sheltered environment for at least 80 minutes and more generally for 80-135 minutes or more than 135 minutes for longer exposure stages.

The screw insertion stage includes a series of screw insertion tasks associated with placing pedicle screws into the vertebral bodies. The screw insertion tasks may vary in screw insertion time and scope depending on the type of procedure and number of instrumented levels. For example, a posterior fusion type of screw insertion task may involve establishing 20 fixation points, which may take more than 60 minutes to perform and typically 60-90 minutes.

In accordance with embodiments herein, the instrumentation in the cabinets, that is unrelated to exposure or screw insertion tasks, remains enclosed and sheltered within corresponding trays and cabinets for an entirety of, not only the entire exposure stage of the surgical procedure, but also the screw insertion stage, thereby maintaining the non-exposure and non-screw insertion related instrumentation in an enclosed and sheltered environment for at least 140 minutes and more generally for 140-225 minutes or more than 225 minutes for longer exposure and/or screw insertion stages.

The rod manipulation and closure stage include a series of rod manipulation and closure tasks including inserting the rods into the screw fixation points, attaching set screws, and using a variety of instruments to manipulate the rod and apply a spine adjustment of interest (e.g., correct the spine). The rod manipulation tasks also include final tightening and break-off of set screws which is performed before last steps of decortication and bone grafting before the final incision closure tasks. The rod manipulation and closure tasks are performed over a rod manipulation and closure time. By way of example, the rod manipulation and closure time may be at least 60 minutes and typically takes approximately 60-90 minutes depending on the size and scope of the procedure.

Thus, as explained herein, the rod manipulation and closure instrumentation in the cabinets, remains in an enclosed and sheltered state within corresponding trays and cabinets for an entirety of, not only the entire exposure stage of the surgical procedure, but also the screw insertion stage, thereby maintaining the rod manipulation and closure related instrumentation in an enclosed and sheltered state and environment for at least 140 minutes and more generally for 140-225 minutes or more than 225 minutes for longer exposure and/or screw insertion stages. The rod manipulation and closure related instrumentation is only exposed to the O.R. environment during the corresponding stage of the procedure, namely up to 60-90 minutes before being utilized. In the foregoing example, a total time estimate for a 10 level fusion is 315 minutes, namely five hours and twenty five minutes.

Figure 11:
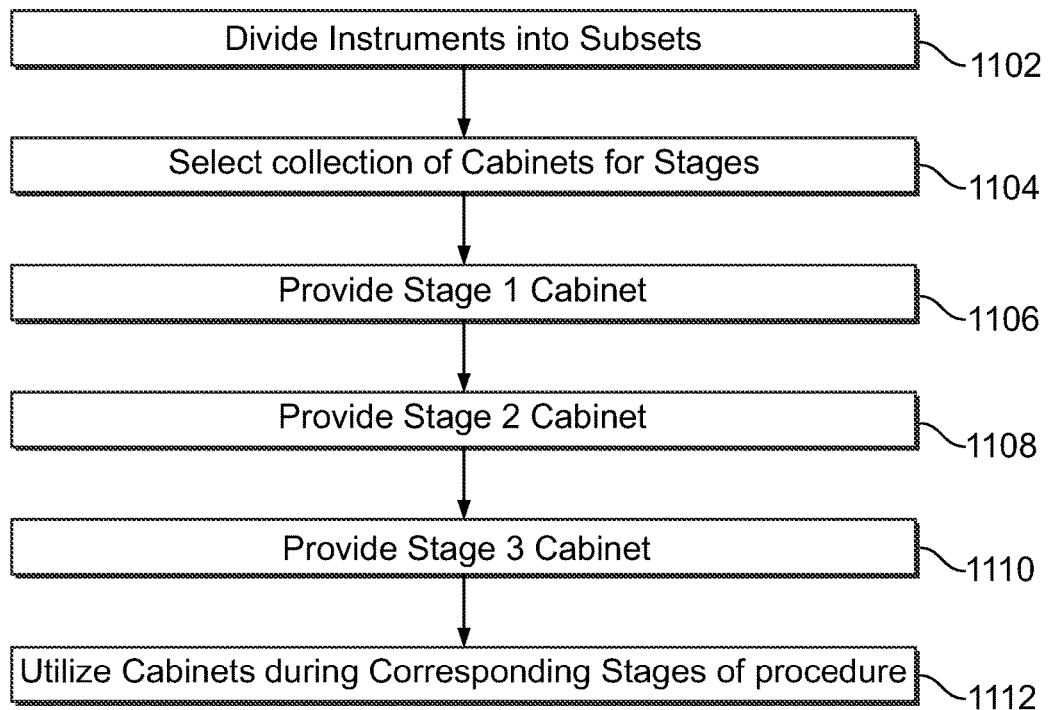
FIG. 11 illustrates a process for organizing a cabinet system to be utilized in a multi-stage surgical procedure in accordance with embodiments herein.

FIG. 11 illustrates a process for organizing a cabinet system to be utilized in a multi-stage surgical procedure in accordance with embodiments herein. In the example of FIG. 11, the multi-stage surgical procedure includes three stages, such as discussed above, namely i) exposure stage, ii) screw insertion (SI) stage and iii) rod manipulation and closure (RMC) stage. At 1102, a set of instruments for the surgical procedure are divided into subsets or collections associated with the corresponding stage.

At 1104, a collection of cabinets are selected and designated for the corresponding stages. For example, the selection may include choosing cabinets that have a desired number of shelves (levels) to receive a desired number of trays. In the present example, a collection (e.g., 3) of two-level cabinets are chosen, where each of the two-level cabinets have a top plate, a bottom shelf and one intermediate shelf there between, to define first and second tray passages that are configured to receive first and second instrumentation retention trays, respectively. The tray passages allow both of the first and second instrumentation retention trays to be inserted into the housing, opened to an open position relative to the housing, and/or entirely removed in at least two directions, and more preferably at least three directions. The collection of cabinets may include 3 two-level cabinets, where each of the three cabinets are assigned and dedicated to be used with a corresponding one of the 3 stages (referred to herein as stage-# cabinet, exposure stage cabinet, etc.).

At 1106, a stage-1 (exposure stage) cabinet is provided that is loaded with instrumentation associated with actions and tasks performed during the exposure stage. For example, the stage-1 cabinet is a 2-level cabinet that includes two wire baskets as the instrumentation trays. The tray passages in the stage-1 cabinet are positioned to allow the instrumentation retention trays therein to be inserted into the housing and opened to an open position relative to the housing through at least one end and at least one side. The two wire baskets are loaded with exposure instruments. For example, the instruments may include osteotomes, pituitarys, rongers, kerrisons, needle driers, mallet. One or more labels may be inserted on one or more side or end walls of the tray and/or on the cabinet housing. The exposure trays may be labeled, such as "Stage 1", "Exposure Stage", "Exposure Instrumentation Tray #1", "Exposure Instrumentation Tray #2", and the like. Additionally or alternatively, the exposure trays may be color coded. Additionally or alternatively, the exposure trays and/or cabinet may be labeled with a list of the instrumentation provide therein.

At 1108, a stage-2 (screw insertion stage) cabinet is provided that is loaded with instrumentation associated with actions and tasks performed during the screw insertion stage. For example, the stage-2 cabinet is a 2-level cabinet that includes two instrumentation trays. The tray passages in the stage-2 cabinet are positioned to allow the instrumentation retention trays therein to be inserted into the housing and opened to an open position relative to the housing through at least one end and at least one side. The two trays are loaded with screw insertion instruments. For example, the instruments in one tray (one level) may include gear shifts, sounders, taps, screw drivers, power handpiece. The instruments in the second tray (second level) may include screws having select diameters (e.g., 5.5, 6.0, 6.5, and 7.5) and select lengths (e.g., 30-55 mm), as well as rods and set screws. The trays may be labeled (e.g., Stage 2, Set Screw Stage, Screw Insertion Tray #1, Screw and Rod Implant Tray #2). One or more labels may be inserted on one or more side or end walls of the tray and/or on the cabinet housing.

At 1110, a stage-3 (rod manipulation and closure stage) cabinet is provided that is loaded with instrumentation associated with actions and tasks performed during the rod manipulation and closure stage. For example, the stage-3 cabinet is a 2-level cabinet that includes two instrumentation trays. The two trays are loaded with rod manipulation and closure instruments. For example, the instruments in one tray (one level) may include a French bender, distractor, compressor, rod pusher, rod grippers, stab and grab, rachet handles, kyphosis and lordosis benders, rocker, blue t-handles, swisel sticks and breakoff counter torque. The second tray (second level) may include any other miscellaneous instruments potentially needed. The trays may be labeled (e.g., Stage 3, Rod Manipulation Stage, Rod Manipulation Tray #1, Miscellaneous Instruments Tray #2). One or more labels may be inserted on one or more side or end walls of the tray and/or on the cabinet housing.

Optionally, the providing operations at 1106-1110 may include positioning the cabinets in the O.R., such as by stacking the cabinets on one another and/or arranging the cabinets adjacent one another in a spaced apart manner, and/or a combination thereof (e.g., stacking 2 cabinets and setting a $3^{rd}$ cabinet at a spaced apart location).

Optionally, the tray passages in the stage-1, stage-2 and/or stage-3 cabinets are positioned to allow the instrumentation retention trays therein to be inserted into the corresponding housings and opened to an open position relative to the corresponding housings through at least three directions.

At 1112, the method utilizes the collection of multi-level cabinets during the surgical procedure. The utilization operation includes opening the instrument retention trays of the stage-1 cabinet during the first stage in one of at least two directions, while maintaining the instrument retention trays of the stage-2 cabinet closed during the first stage. For example, the at least two directions may include at least one end and at least one side of the housing. The utilization operation further includes maintaining the instrument retention trays of the stage-1 and stage-2 cabinets closed until one or more of the instruments in a corresponding one of the instrument retention trays is needed for use in the surgical procedure to reduce a potential for contamination. By way of example, the surgical procedure includes an exposure stage, a screw insertion stage and a rod manipulation stage. The multi-level cabinets include at least one instrument retention tray that includes rod manipulation instruments for use during the rod manipulation stage. The utilization operation comprises maintaining the at least one instrument retention tray, that includes the rod manipulation instruments, in a closed and sheltered environment within the corresponding multi-level cabinet until the surgical procedure advances to the rod manipulation stage.

During a surgical procedure in the OR, the three cabinet collection may be stacked on top of one another in a predetermined order in or a random order. For example, the cabinets may be stacked with Stage 1 on top, Stage 2 in the middle and Stage 3 on the bottom, such that as instruments are removed the overall stack of cabinets becomes lighter from the top down over the progression of the surgical procedure. Optionally, the cabinets may be stacked with Stage 3 on top, Stage 2 in the middle and Stage 1 on the bottom. Optionally, the cabinets may be stacked based on weight such that the heaviest cabinet is on the bottom. Optionally, the cabinets may be stacked such that the cabinet least used is on the top (or in whichever position is least convenient), while the cabinet most used is at a level most convenient.

Optionally, during the surgical procedure, the cabinet collection may be arranged side by side immediately adjacent one another or spaced apart from one another with sufficient space therebetween to allow a tray to be opened in a direction between the cabinets.

The collection of cabinets provide a substantially savings in "real estate" needed for set up in an O.R setting as compared to a convention OR set up. When stacked in a single vertical stack, the cabinets only occupy the space of one, two or three instrumentation trays, as the remainder of the trays are stacked in a closed position and locked on top of one another, but with the ability to access all six levels from any direction. Embodiments herein significantly reduce "Set up" time as outlined above, as the medical personnel no longer need to set out every tray with every instrument for the entire procedure and no longer need to reorganize a large number of trays spead over an OR. Embodiments herein avoid a need for placing instrumentation in a particular order or spacing out of instruments across an OR area.

Embodiments herein substantially reduce a risk of instrument contamination that is experienced in convention instrument usage as the cabinets herein retain unused instruments in an enclosed and sheltered state or environment until used or until at least a select stage of the procedure. The cabinets afford the ability to "house" instruments until needed, therefore reducing time of exposure of instrumentation during all portions of the stages of the procedures described herein.

Optionally, embodiments herein may standardize cabinets and trays with a predetermined organization of tray order and the instrumentation in the trays for a more efficient delivery to the O.R. theater.

Figure 12:
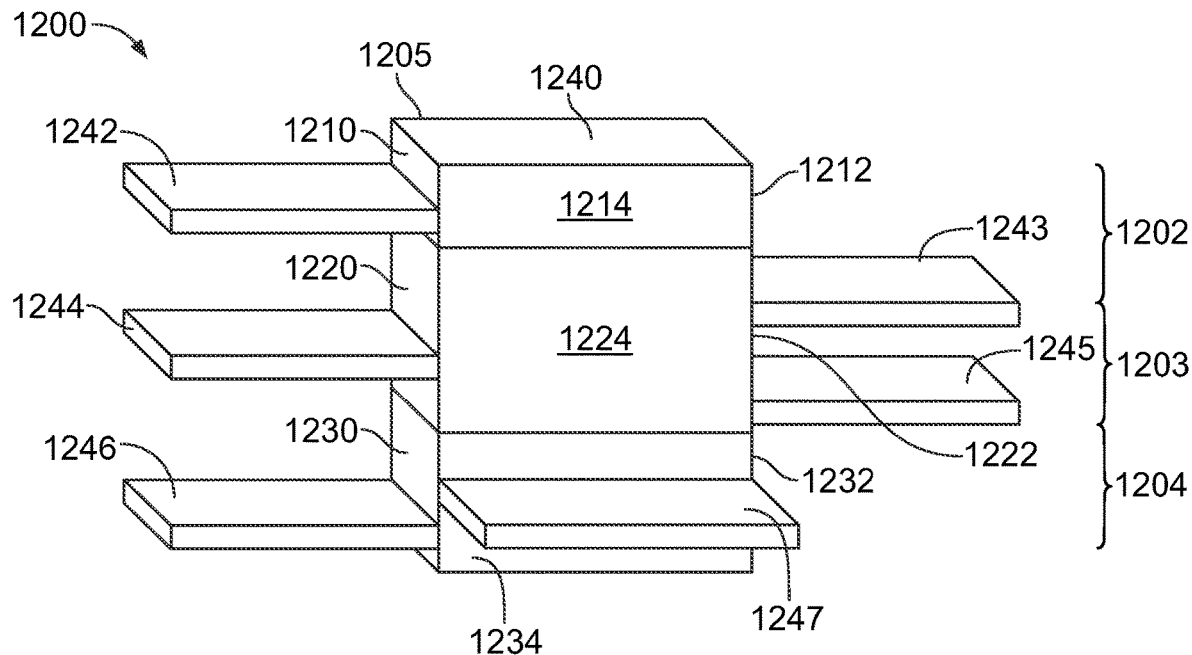
FIG. 12 illustrates a front perspective view of a cabinet system joined to one another in an O.R. in accordance with an embodiment herein.

FIG. 12 illustrates a front perspective view of a cabinet system 1200 joined to one another in an O.R. in accordance with an embodiment herein. The cabinet collection 1200 includes a stage-1 multi-level cabinet 1202, a stage-2 multi-level cabinet 1203 and a stage-3 multi-level cabinet 1204. Each of the cabinets 1202-1204 includes front sides 1214, 1224, 1234, back sides (not shown), and opposite ends 1210, 1212, 1220, 1222, 1230, and 1232. Each of the cabinets 1202-1204 comprise a housing including a top plate, a bottom shelf and at least one intermediate shelf there between. The housing separates the intermediate shelf from the top plate and bottom shelf to define first and second tray storage areas there between. The first and second tray storage areas are configured to receive the first and second instrumentation retention trays, respectively. The housing includes tray passages located on at least a side and an end of the housing. The tray passages communicate with the first and second tray storage areas to allow all of the instrumentation retention trays 1240-1247 to be inserted into the corresponding cabinet housing and opened to an open position relative to the housing in at least two directions. Optionally, the trays 1240-1247 may be removed entirely from the corresponding cabinet housing.

The cabinets 1202-1204 include instrumentation retention trays 1240-1247 that are loaded with instrumentation use in connection with first, second and third stages, respectively, of a surgical procedure. For example, the stage-1 cabinet 1202 is provided with instrumentation retention trays loaded with instrumentation for use with actions or tasks performed during the first stage of the surgical procedure. The stage-2 cabinet 1203 is provided with instrument retention trays loaded with instrumentation for use with actions or tasks performed during the second stage of the surgical procedure. The stage-3 cabinet 1204 is provided with instrument retention trays loaded with instrumentation for use with actions or tasks performed during the second stage of the surgical procedure. By way of example, the term "providing" may include loading the instruments in the instrumentation retention trays and loading the instrumentation retention trays into the stage-1 and stage-2 cabinets. Additionally or alternatively, the term "providing" may merely refer to taking possession of, and/or using, a pre-loaded tray or cabinet. For example, the use of the cabinets 1202-1204 during a surgical procedure represents one example of how the cabinets 1202-1204 are provided with the trays 1240-1247.

In the example of FIG. 12, the stage-1, stage-2 and stage-3 cabinets are stacked on one another. A top 1205 of the stage-1 cabinet 1202 is opened or removed to allow access to the tray 1240, while tray 1242 is slid out of the end 1210 of the cabinet 1202, during the first stage of the surgical procedure. Once the first stage is complete, the top 1204 may be closed and the tray 1242 may be closed. During the first stage, the trays 1243-1247 remain closed in an enclosed and sheltered environment within housings of the cabinets 1203 and 1204. During the second stage of the procedure, one, two or all three of trays 1243-1245 are opened through the front/back sides and/or opposite ends 1220, 1222, depending on the number of passages provided in the cabinet 1203. In the present example, the trays 1243-1245 are opened through opposite ends 1220, 1222. During the second stage, the trays 1246-1247 of the third stage cabinet 1204 remain closed in an enclosed and sheltered environment within housings of the cabinet 1204. After stage 2, during the third stage of the procedure, one or both of trays 1246-1247 are opened through the front/back sides and/or opposite ends 1230, 1232, depending on the number of passages provided in the cabinet 1204. The tray 1246 is slid out from one end and the tray 1247 is slid out through the front 1234.

The single cabinets and cabinet systems described herein retain the instrumentation retention trays closed in an enclosed and sheltered environment within the cabinet for a substantial portion of the medical procedure, only opening the trays at or near the time when the instruments therein are to be used. By reducing the amount of time in which the instruments are exposed to the environment of the operating room or other clinical area, embodiments herein substantially reduce the exposure time to contaminants within the environment and substantially reduce the level of contamination experienced by such instruments prior to usage. As explained above, conventional systems expose all of the instruments for the entire surgical procedure which may last several hours. In contrast, the cabinets, systems and methods herein allow medical personnel to keep the instruments in an enclosed and sheltered environment until used, or at least until a corresponding stage of a multi-stage surgical procedure.

Optionally, trays may be marked with indicia indicative of a content of the tray. For example, when trays are organized for particular aspects of the procedure, the corresponding aspect may be indicated on the tray. For example, the indicia may indicate color coding, descriptive text, numbers, and the like. The indicia may be included on all or a portion of the sidewalls of the tray. Optionally, when components of the cabinet are formed with aluminum, the component may anodized to afford protection. Optionally, the anodization process may be used to color code areas or complete trays, to include indicia on the tray. Optionally, color coding and other graphical indicia may be provided on the interior surfaces of the baseplates within the trays. For example, indicia may be used to define outlines or locations for particular types of instrumentation, thereby facilitating organization and reloading of an empty tray. In addition, by providing indicia indicative of individual tools, embodiments herein afford the ability to provide an indicator to surgical personnel when a particular instrument, implant and the like has been removed from a particular tray.

Optionally, embodiments herein may include a cabinet structure having shelves that are dimensioned and spaced apart to receive pre-existing trays therein. For example, a first cabinet may be constructed to receive existing trays (including existing wire baskets) built by a first manufacturer and/or a first type of tray, while another cabinet may be constructed to receive existing trays built by another manufacturer. Alternatively, a cabinet may be billed to have different heights between the shelves where the heights are configured to receive existing trays having different side profiles/fights.

In accordance with at least one embodiment, the tray base and shelves are formed with a generally planar alignment. However, optionally, the tray bases and shelves may be formed in alternative manners to add rigidity, such as in central portions of one or more of the tray bases and shelves. For example, the tray base and/or shelves may be stamped or otherwise shaped to include a non-flat geometry to increase a rigidity of the tray and/or shelf. For example, a center portion of the shelves and/or trays may be stamped to include ridges, ribs, waves or another non-flat geometry. The height of the added structure may vary, such as molding and or stamping in a quarter inch high ridge along a flat surface area of the shelf and/or tray base. Optionally, different combinations of materials may be utilized for the trays, shelves, corners and/or edges to add strength while reducing weight. As a further option, added structural components may be mechanically attached to the tray bases and/or shelves, such as by adding separate ribs, crossbeams, and the like. As yet a further example, the added structural components may simply represent second, third or fourth layers of the same material used to form the tray base and/or shelves, with the secondary layers covering all or only select portions of the main tray base and/or shelves.

It is recognized that the embodiments herein may be implemented in various types of medical settings and medical procedures, including, but not limited to spine, ear nose throat, cardio, eye surgery, plastic surgery and the like. The cabinets described herein afford the benefits that include, among other things, a time savings in connection with preparing an operating room as well as locating instruments desired by a physician, cost savings, safety, flexibility and reduction in contamination.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A medical instrumentation storage cabinet comprising:
    first and second instrumentation retention trays configured to receive instrumentation;
    a housing including a top plate, a bottom shelf and at least one intermediate shelf there between, one or more of the top plate, the bottom shelf, the intermediate shelf or the first and second instrumentation retention trays including a plurality of holes there through to allow passage of a sterilization medium during a sterilization process, the housing having a front, back and opposite ends; and
    the intermediate shelf separated from the top plate and bottom shelf to define first and second tray storage areas there between, the first and second tray storage areas configured to receive the first and second instrumentation retention trays, respectively; and
    the housing including tray passages to the first and second tray storage areas, the tray passages located in the front and in at least one of the ends of the housing, the tray passages located to allow both of the first and second instrumentation retention trays to be inserted into the housing and opened to an open position through the front and through the at least one of the ends.

2. The cabinet of claim 1, wherein the tray passages are located in each of the ends of the housing to allow inserting and/or opening the first instrumentation retention tray through a first end of the housing and an opposite second end of the housing.

3. The cabinet of claim 1, wherein one of the tray passages is located in a back of the housing to allow inserting and/or opening the first instrumentation retention tray through the back of the housing.

4. The cabinet of claim 1, wherein the tray passages are adapted to allow inserting and/or opening the first instrumentation retention tray through the front and at least a first end; and to allow inserting and/or opening the second instrumentation retention tray through the front and at least a second end of the housing.

5. The cabinet of claim 1, wherein the top plate, bottom and intermediate shelfs and first and second instrumentation retention trays are formed of a sterilization tolerant material.

6. The cabinet of claim 1, further comprising instrumentation within the first and second instrumentation retention trays.

7. The cabinet of claim 6, wherein the instrumentation includes a first set of instrumentation in the first instrumentation retention tray corresponds to a first aspect of the predetermined procedure and a second set of instrumentation in the second instrumentation retention tray corresponds to a second aspect of the predetermined procedure.

8. The cabinet of claim 7, further comprising indicia on the first and second instrumentation retention trays, the indicia including at least one of color coding, descriptive text, or numbers to indicate a content thereof.

9. The cabinet of claim 1, wherein the top plate and bottom shelf include rails formed along side and end edges thereof, the rails on the top plate facing and aligning with the rails on the bottom shelf, the housing further comprising side and end doors slidably received within the corresponding rails, the side and end doors sliding between open and closed positions to expose and cover the tray passages.

10. The cabinet of claim 1, wherein the top plate includes an opening therein, the cabinet further comprising a lid configured to open and close the opening.

11. A medical instrumentation storage cabinet for first and second instrumentation retention trays, the cabinet comprising:
    a housing including a top plate, a bottom shelf and at least one intermediate shelf there between, one or more of the top plate, the bottom shelf, or the intermediate shelf including a plurality of holes there through to allow passage of a sterilization medium during a sterilization process,
    the housing including a front, a back and opposite first and second ends,
    first and second tray storage areas between the intermediate shelf, the top plate and bottom shelf;
    tray passages to the first and second tray storage areas, the tray passages located in the front and in at least one of the first or second ends of the housing, the tray passages adapted to allow the first and second instrumentation retention trays to be inserted into the housing and opened to an open position through the front and through at least one of the first or second ends.

12. The cabinet of claim 11, wherein the tray passages are located in each of the first and second ends of the housing.

13. The cabinet of claim 11, wherein one of the tray passages is located in the back of the housing.

14. The cabinet of claim 11, wherein the tray passages are adapted to allow insertion and/or opening the first instrument retention tray through the front and at least the first end of the housing and insertion and/or opening the second instrumentation retention tray through the front and at least the second end of the housing.

15. The cabinet of claim 11, wherein the top plate, bottom and intermediate shelfs are formed of a sterilization tolerant material.

16. The cabinet of claim 11, further comprising the first and second instrumentation retention trays.

17. The cabinet of claim 16, further comprising instrumentation including at least one of surgical instruments or implants to be stored in at least one of the first and second surgical instrument retention trays.

18. A medical instrumentation storage system comprising:
instrumentation;
first and second instrumentation retention trays configured to receive the instrumentation;
a cabinet including a housing including a top plate, a bottom shelf and at least one intermediate shelf there between, one or more of the top plate, the bottom shelf, the intermediate shelf or the first and second instrumentation retention trays including a plurality of holes there through to allow passage of a sterilization medium during a sterilization process, the housing having a front, back and opposite ends; and
the intermediate shelf separated from the top plate and bottom shelf to define first and second tray storage areas there between, the first and second tray storage areas configured to receive the first and second instrumentation retention trays, respectively; and
the housing including tray passages to the first and second tray storage areas, the tray passages located in the front and in at least one of the ends of the housing, the tray passages located to allow both of the first and second instrumentation retention trays to be inserted into the housing and opened to an open position through the front and through the at least one of the ends.

19. The system of claim 18, further comprising first and second cabinets configured to be stacked on top of one another.

20. The system of claim 19, further comprising first and second instrumentation in the first and second instrumentation retention trays, respectively of the first cabinet and third and fourth instrumentation in third and fourth instrumentation retention trays, respectively, of the second cabinet.

* * * * *